(12) United States Patent
Gustafsson

(10) Patent No.: US 11,723,806 B2
(45) Date of Patent: Aug. 15, 2023

(54) FILM ROLL, AND A FILM ADVANCE SYSTEM AND PROTECTIVE GOGGLES COMPRISING SUCH A FILM ROLL

(71) Applicant: FASTIGHETSVISION BYGG & ENTREPRENAD 01 AB, Osby (SE)

(72) Inventor: André Gustafsson, Osby (SE)

(73) Assignee: FASTIGHETSVISION BYGG & ENTREPRENAD 01 AB, Osby (SE)

( * ) Notice: Subject to any disclaimer, the term of this patent is extended or adjusted under 35 U.S.C. 154(b) by 0 days.

(21) Appl. No.: 16/507,600

(22) Filed: Jul. 10, 2019

(65) Prior Publication Data

US 2021/0007895 A1    Jan. 14, 2021

(51) Int. Cl.
| | | |
|---|---|---|
| *A61F 9/02* | (2006.01) | |
| *B08B 1/00* | (2006.01) | |
| *A42B 3/26* | (2006.01) | |

(52) U.S. Cl.
CPC ............... *A61F 9/029* (2013.01); *A42B 3/26* (2013.01); *A61F 9/025* (2013.01); *B08B 1/006* (2013.01)

(58) Field of Classification Search
CPC . A61F 9/029; A61F 9/025; A42B 3/26; Y10S 242/912; B65H 2301/41522; B65H 2301/41524
USPC ........................ 2/426, 438; 242/912; 116/278
See application file for complete search history.

(56) References Cited

U.S. PATENT DOCUMENTS

| | | | | |
|---|---|---|---|---|
| 4,428,081 A | * | 1/1984 | Smith ..................... | A61F 9/025 2/8.1 |
| 7,793,608 B1 | * | 9/2010 | Udouj .................... | B65H 18/28 242/165 |
| 9,839,558 B2 | | 12/2017 | Blanchard et al. | |
| 2014/0157496 A1 | * | 6/2014 | Ginther .................... | A61F 9/02 2/439 |

(Continued)

FOREIGN PATENT DOCUMENTS

| | | |
|---|---|---|
| EP | 2944297 A | 11/2015 |
| GB | 2378412 A | 12/2003 |
| GB | 2495984 A | 5/2013 |

OTHER PUBLICATIONS

POS Supply Solutions Blog, dated Jan. 29, 2019, retrieved by Examiner on Oct. 21, 2021 at https://www.possupply.com/end-of-roll-warning-stripe (Year: 2019).*

(Continued)

*Primary Examiner* — F Griffin Hall
(74) *Attorney, Agent, or Firm* — Fulwider Patton LLP

(57) ABSTRACT

A film roll for use in a film advance system for eye protective goggles comprises a transparent film wound on the spindle. The film has an inner trailing end, a leading end, and a total film length. In use, the transparent film extends across a lens of the goggles. The transparent film presents a transparent main film part, which extends in the longitudinal direction from the trailing end to the leading end, and which presents optically uniform characteristics at least in the longitudinal direction. The transparent film is provided with at least one visual indication, which is located above the main film part and extends along an upper film edge of the transparent film, said at least one visual indication being limited to a trailing part of said total film length.

44 Claims, 10 Drawing Sheets

(56) References Cited

U.S. PATENT DOCUMENTS

2017/0313543 A1 11/2017 Kulik
2017/0354540 A1 12/2017 Yang et al.

OTHER PUBLICATIONS

PCT/EP2019/068515—Int'l Search Report.
PCT/EP2019/068515—Written Opinion.
PCT/EP2019/068515—PCT Publication.

* cited by examiner

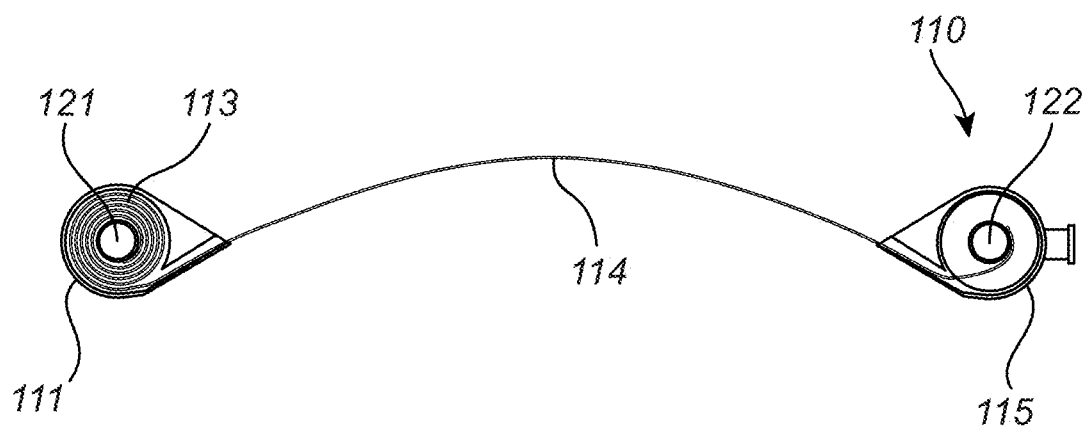
*Fig. 1CB*
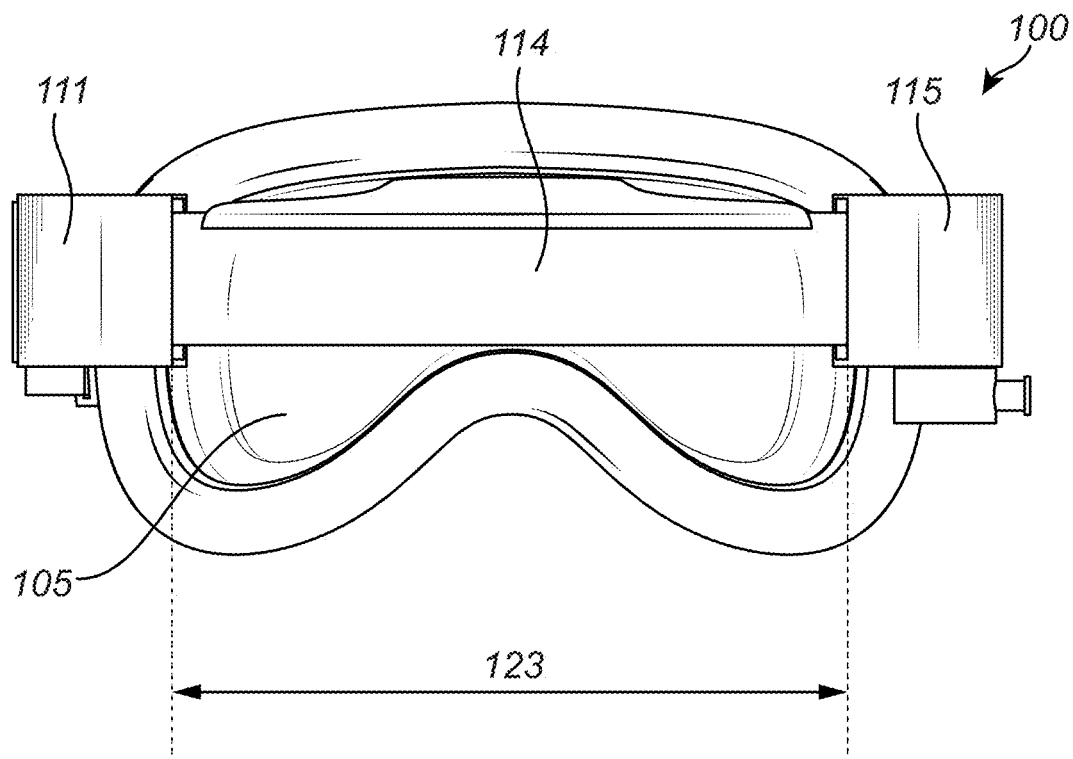
(Prior art) *Fig. 1CA*

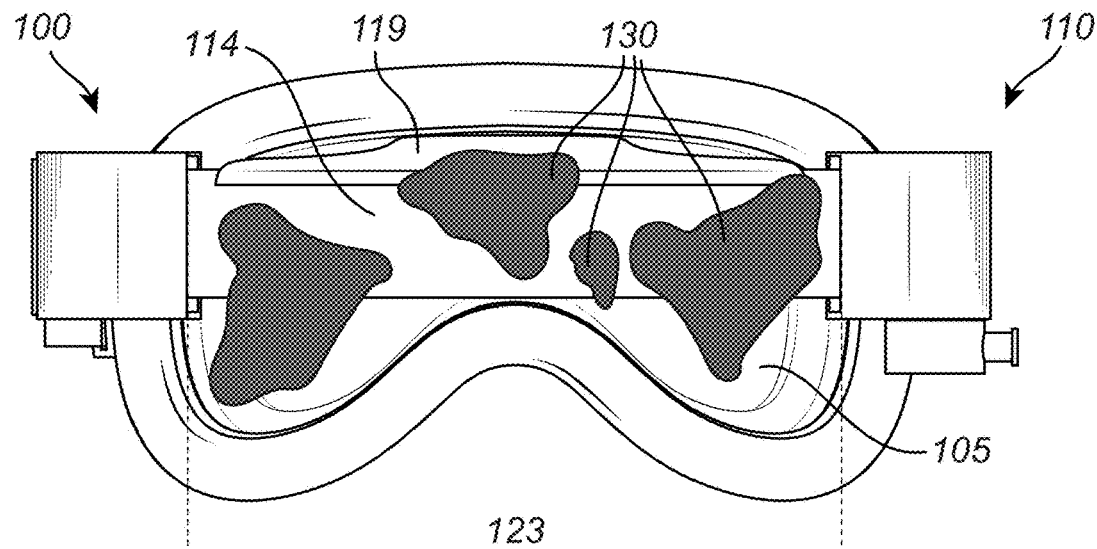
(Prior art) *Fig. 2A*
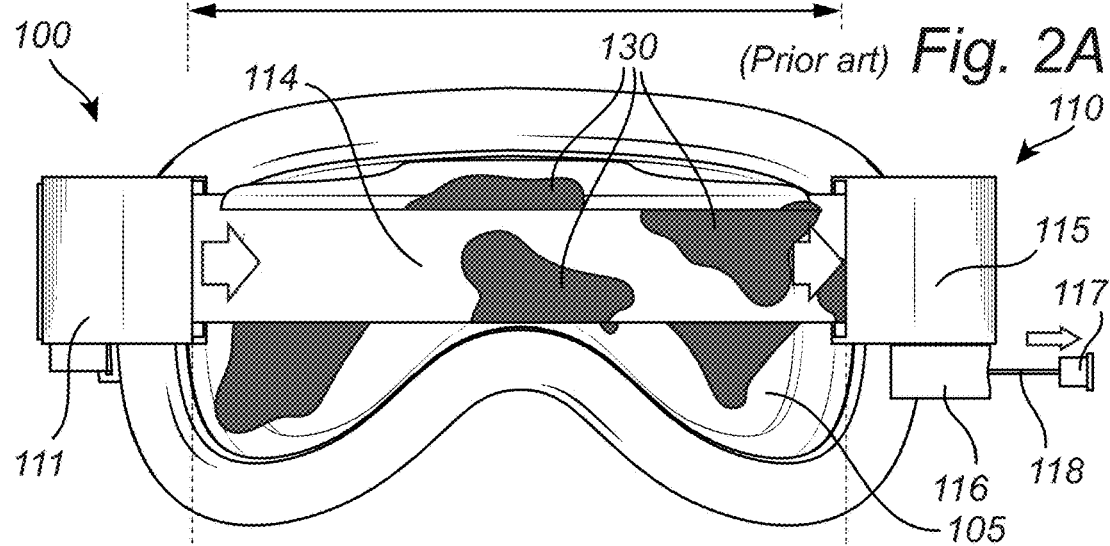
(Prior art) *Fig. 2B*
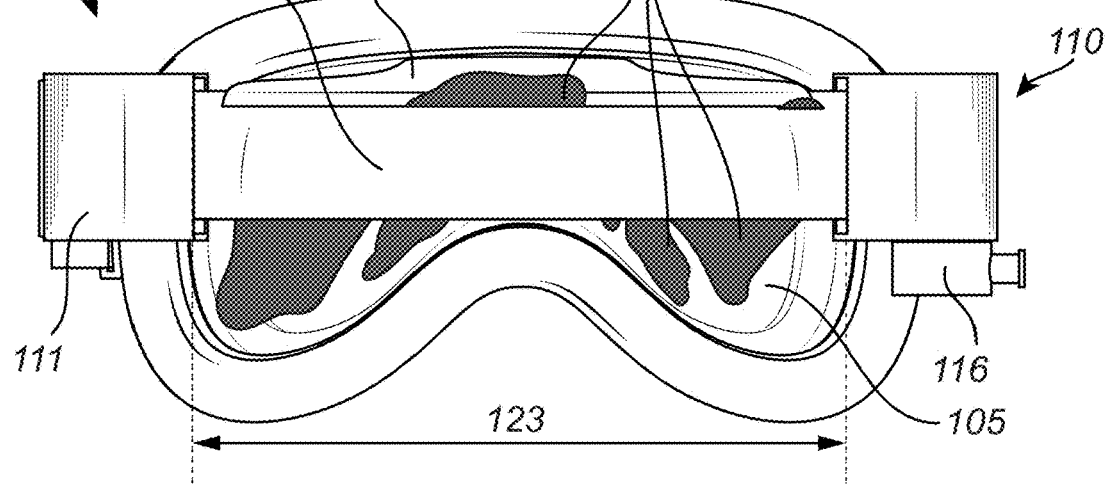
(Prior art) *Fig. 2C*

FILM ROLL, AND A FILM ADVANCE SYSTEM AND PROTECTIVE GOGGLES COMPRISING SUCH A FILM ROLL

REFERENCE TO RELATED APPLICATION

This application is related to PCT Application No. PCT/EP2019/068515, entitled "A Film Roll, And A Film Advance System And Protective Goggles Comprising Such A Film Roll," filed Jul. 10, 2019, which is incorporated by reference in its entirety.

TECHNICAL FIELD

The present disclosure generally relates to the field of eye protective goggles, and in particular to a film roll for use in a film advance system for eye protective goggles, a film advance system and eye protective goggles including such a film roll.

BACKGROUND

Goggles are commonly used to protect the human eyes in a variety of different activities, there among motorcycle racing, snow sports, watersports, and biking. Particularly in activities involving off-road vehicles, such as motorcycle racing, goggles are worn by the driver for protecting the eyes against splashing mud, dirt and rocks. Hence forth the description and explanations given in the present text are based on the example of the user being a driver in a motorcycle race, although such goggles may be used also in other activities.

One drawback with standard goggles is that mud and dirt remains on the goggle lens, blocking the driver's vision. To overcome this problem, goggles equipped with film advance systems are commonly used today. The film advance system enables the driver to maintain a clear vision without the need for interrupting the race to clean the lens, which could otherwise be required several times during a single race. Examples of prior-art goggles equipped with film advance systems are disclosed in US 2015/0328049 A1, U.S. Pat. No. 4,428,081, and GB 2 378 412.

Goggles equipped with a film advance system comprise a roll of flexible, transparent film in a film supply magazine arranged on one of the lateral sides of the lens. On the opposite lateral side of the lens, a film take-up magazine is arranged. Once the film roll is installed and ready for use, the transparent film extends across the lens from the supply magazine to the take-up magazine. The take-up magazine is connected to a film advance mechanism that enables the driver, when the driver's vision becomes blocked, to advance the transparent film across the lens in the direction from the supply magazine to the take-up magazine. Hereby, the dirty film section is moved away from the lens into the take-up magazine, and replaced by a clean film section from the supply magazine, restoring clear vision through the goggle lens. Different implementations of film advance mechanisms are available. One commonly used mechanism is activated by the driver manually pulling a knob at the end of a flexible cord connected to a mechanical actuator, winding a used film section into the take-up magazine. The mechanical actuator may be a ratchet-type device allowing rotatory motion in one direction only. The ratchet-type device prevents the film from subsequently being wound off of the spindle in the take-up magazine, when the driver has released the knob and the cord is retracted back into the mechanical actuator. Also, electrically activated advance mechanisms are available.

Although such prior-art goggles provided with film advance systems are advantageous in many aspects, there is still a need for further improvements.

SUMMARY OF THE INVENTION

According to a first aspect of the inventive concept, there is provided a film roll for use in a film advance system for eye protective goggles. The film roll comprises:
  a spindle; and
  a transparent film being wound on the spindle and having an inner trailing end, a leading end, and a total film length extending in a longitudinal direction between the trailing end and the leading end, wherein in use the transparent film is arranged to extend across a lens of the goggles;
  wherein the transparent film presents a transparent main film part constituting a major part of the transparent film, said main film part extending in the longitudinal direction from the trailing end to the leading end, and presenting optically uniform characteristics at least in the longitudinal direction; and
  wherein the transparent film is provided with at least one visual indication, which is located above the main film part and extends along an upper film edge of the transparent film, said at least one visual indication being limited to a trailing part of said total film length.

According to a second aspect of the inventive concept, there is provided a film roll for use in a film advance system for eye protective goggles. The film roll comprises a spindle, and a transparent film being wound on the spindle and having a trailing end, a leading end, a height extending in a vertical direction, and a total film length extending in a longitudinal direction from the trailing end to the leading end, whereby in use the transparent film is arrangeable to extend across a lens of the goggles. Further, the transparent film has three planar parts, being: a main part which extends longitudinally over the total film length and vertically over a lower 50% of the height; an upper leading part which extends longitudinally from the leading end to a center of the total film length, and vertically over an upper 50% of the height; an upper trailing part which extends longitudinally from the center of the total film length to the trailing end, and vertically over an upper 50% of the height. Under the foregoing, the main part has optically uniform characteristics at least in the longitudinal direction; furthermore, the upper leading part may also have optically uniform characteristics at least in the longitudinal direction; the upper trailing part has at least one visual indication that extends along an upper edge of the transparent film; and the at least one visual indication is excluded from the main part and from the upper leading part.

According to a third aspect of the inventive concept, there is provided a film advance system for eye protective goggles. The film advance system comprises:
  a film roll according to the first aspect of the inventive concept, or the second aspect of the inventive concept,
  a film supply magazine for said film roll,
  a film take-up magazine, and
  a film advance mechanism for advancing the transparent film of the film roll from the film supply magazine to the film take-up magazine.

According to a fourth aspect of the inventive concept, there is provided eye protective goggles, comprising a lens and a film advance system according to the third aspect of the inventive concept, wherein the film supply magazine and the film take-up magazine of the film advance system are located on opposite lateral sides of the lens, and wherein said film advance mechanism of the film advance system is arranged to advance the transparent film of the film roll over a front surface of the lens.

According to a fifth aspect of the inventive concept, there is provided a method for warning a motor-cyclist who is wearing goggles, the goggles having a lens and being equipped with a supply magazine containing a film which is transparent and has a length and a height and which extends across the lens, the method comprising:

winding the film from a supply spindle onto a take-up spindle;

warning the motor-cyclist that a limited amount of film remains on the supply spindle;

wherein, warning the motor-cyclist includes advancing, across the lens, a film on which there is a visual indication.

Preferred embodiments of the inventive concepts are set out in the dependent claims.

The inventive concepts present at least the following advantage over the prior-art. If the driver runs out of film before the race is finished, the driver may need to take off the goggles in order to see, but finishing a motorcycle race without goggles is dangerous and can be harmful to the eyes, besides the race-related disadvantage. With the present inventive concept, this can be avoided in most situations. The present inventive concept enables to provide an early warning to the driver, well before running out of film, that a limited length of film remains in the supply magazine, i.e. that a limited number of clean film sections remain. Once the visual indication appears through the lens, it will serve as a warning to the driver that only a limited number of further film advancements is possible. This warning gives the driver the chance to save film by tactic driving in order to avoid advancing the film so often, in order to avoid running out of film before the race is finished. Thus, the warning is valuable to the driver in terms of planning the race as well as the use of film for the remaining part of the race. Accordingly, the visual indication should initially appear as a warning before the supply magazine runs out of clean film, and not when the film roll is actually empty.

In the present disclosure, the term "transparent" refers to the physical material property of allowing light to pass through the material without being substantially scattered, such that it is possible to see clearly through the material. In some embodiments, the transparency may be substantially uniform over the spectrum of visible light, such that colors viewed through the transparent material are essentially unaltered. Alternatively, the transparency may vary as a function of light wavelength over the visible part of the spectrum, such that the view thought the transparent material is tinted in one or more colors.

In the present disclosure, the term "film" refers to a strip of a flexible material, extending in a longitudinal direction of the film between a leading film end and a trailing film end. By way of example, the flexible material from which the film is made, may be, but is not limited to, a plastic material.

In the present disclosure, "optically uniform characteristics" refers to the optical properties of the film material are visually constant over the relevant area of the film. Given as non-limiting examples, such properties may be transparency, reflectivity and color. The effect of having a main film part with optically uniform characteristics is that there are no noticeable changes in the appearance of the main film part to the eyes of the driver. Consequently, the main film part is free from elements that may be disturbing or obstructing to the vision of the driver.

In the present disclosure, "visual indication" refers to a change in the visual appearance of the transparent film that enables the driver to see the difference between the beginning of the trailing part of the film that includes the "visual indication" and the preceding part of the film. This visual contrast between the beginning of the trailing film part and the preceding part of the film enables the driver to distinguish between the two parts. Thereby, a warning is provided to the driver that a limited number of clean film sections are left on the film roll in the supply magazine before the end of the film roll is reached.

Embodiments of the Inventive Concept

In preferred embodiments, the visual indication is limited to a trailing part of said total film length, in the sense that said visual indication has a total length along the upper film edge which is 50% or less of said total film length. In this manner, the visual indication is not present on the first half of the film, having the advantageous effect the driver is not warned until at least half of the transparent film on the film roll is used. The driver can therefore use a major part of the film without being warned. The warning is normally not relevant for the user until a major part of the transparent film has been used.

In some embodiments, the visual indication is limited to a trailing part of said total film length, in the sense that said total length of the visual indication is 20% or less of said total film length.

In some embodiments, the visual indication is limited to a trailing part of said total film length, in the sense that the trailing part corresponds to a limited certain number of remaining clean film sections, each section corresponding in length to the width of the lens of the goggles. As a non-limiting example, a full film roll having total of 100 clean available sections may have a warning appearing when say 20 clean sections remain, while a larger or longer full film roll having a total of 150 clean available sections may have a warning also appearing when say 20 clean sections remain. In this illustrative example, the two film rolls of different length would provide the warning corresponding to the same number of remaining clean film sections.

In some embodiments, the visual indication has a total length which is at least 5 times, preferably at least 10 times the lens width between the supply magazine and the take-up magazine.

An advantage of this solution is that the driver may know how many advancements of the film there are left on the film roll, when the visual indication first appears. The wearer may thus be able to plan the remaining part of the race and how many times the lens can be cleaned before running out of film.

In some embodiments, the visual indication extends continuously in the longitudinal direction of the film, along the upper film edge.

An advantage of this solution of a continuous visual indication may be that the visual indication is perceived as less disturbing to the driver. This may prevent the driver from losing focus on the terrain and other drivers along the race track.

In some embodiments, the visual indication extends discontinuously along the upper film edge.

An advantage of this solution of a discontinuous visual indication may be that it may be more noticeable to the driver.

A mix of continuous and discontinuous visual indications is also possible.

In some embodiments, the visual indication comprises a continuous line extending over a total length of the visual indication.

In some embodiments, the visual indication comprises a dashed line.

In some embodiments, the visual indication is at least in part a dotted visual indication.

In some embodiments, the visual indication is substantially uniform along a total length of the visual indication. The visual indication may be uniform with respect to several parameters, as for example height, width, translucency, color or other parameters. The visual indication may be uniform with respect to one or more parameters simultaneously. By way of example, the visual indication may have constant height and be of only one color, but may comprise interruptions as for example being a dashed line.

In some embodiments, the visual indication has a constant height along a total length of the visual indication. An advantage may be that the visual indication operates as a warning while not being too disturbing to the driver. This may prevent the driver from losing focus on the terrain and other drivers along the race track.

In some embodiments, the visual indication has a varying height along its length.

A special advantage of this solution is that the height of the visual indication may be related to the amount of film left in the supply magazine. Given only as an example, the height of the visual indication may increase or decrease, gradually or stepwise, as the end of the film on the film roll is approaching. This may provide the driver with not only a single warning that a limited film amount remains, but also quantitative information about if the end of the film is critically close, or if there is still some film on the roll for cleaning the lens a few more times.

In some embodiments, said at least one visual indication comprises a plurality of visual indications extending along the upper film edge, and having mutually different total lengths.

In some embodiments comprising a plurality of visual indications, the plurality of visual indications comprises a first visual indication being limited to a first trailing part of said total film length, and a second visual indication being limited to a second trailing part of said total film length, wherein the second trailing part is shorter than the first trailing part, and is at least partly overlapping with the first trailing part.

Each visual indication in the plurality of visual indications may serve as a specific warning that the end of the film is approaching. In such embodiments, the driver will get a plurality of warnings as the transparent film across the lens gets closer and closer to the end of the film. Given as a non-limiting example, the first visual indication and the second visual indication may extend from positions of 20% and 10%, respectively, from the trailing film end, such that the driver will first observe the first visual indication when 10-20% of the film is left, while the driver will observe both the first and the second visual indication at the same time when subsequently only 0-10% of the film is left.

In some embodiments, the visual indication is translucent in its entirety or in part.

In the present disclosure, the term "translucent" refers to the physical material property of allowing at least some light to pass through the material. Light may be scattered either at one or both surfaces of the material, or when passing through the material, or a combination thereof. If the light is scattered, it is not possible to see clearly through the material. Light may also pass through the material without being substantially scattered, such that it is possible to see clearly through the material. This case is a subset to "translucent", also referred to as "transparent". In other words, the term "translucent" also encompasses "transparent".

A translucent visual indication will thus allow some of the ambient light to shine through the visual indication, which will have the effect that the visual indication will not merely appear as a shadow to the driver. A special advantage of this solution is that the visual indication may be more clearly visible to the driver. It may also be easier for the driver to distinguish the visual indication from other goggle parts also located close to the eyes of the driver.

The visual indication may be translucent "in part". Given as a non-limiting example, the visual indication may have alternating translucent and non-translucent segments in the longitudinal direction of the film. If the visual indication is a continuous, solid line, but with alternating translucent and non-translucent segments, the line may appear to alternate between dark and bright segments. The alternation may also be in the transvers direction of the film. It may also be that the visual indication starts out as being non-translucent and towards the end of the film becomes translucent, or vice versa. The effect may be that the visual indication is more noticeable to the driver.

In some embodiments, the visual indication is frosted in its entirety or in part.

In the present disclosure, the term "frosted" refers to the physical material property of allowing at least some light to pass through the material, in such a way that the light is scattered. Light may be scattered either at one or both surfaces of the material, or when passing through the material, or at a combination thereof. If the light is scattered, it is not possible to see clearly through the material.

In some embodiments, the visual indication is colored in its entirety or in part.

An advantage of this solution is that it may be easier for the driver to distinguish a colored visual indication from other goggle parts also located close to the eyes of the driver, than compared to a non-colored visual indication.

In some embodiments, the visual indication is red in its entirety or in part.

A special advantage of this solution is that a red color may not be frequently occurring in the typical environment surrounding the driver. Given as an example, in an off-road motorcycle race, the typical surroundings may comprise a blue sky or green vegetation. Thus, it is likely that that it is easier for the driver to distinguish the visual indication from the surrounding environment in the field-of-view, if the visual indication is colored red.

In some embodiments, the visual indication is white in its entirety or in part.

In such embodiments, it may be easier for the driver to distinguish the visual indication from the surrounding environment in the field-of-view, if the visual indication is white, compared to if the visual indication has a darker shade.

In some embodiments, the visual indication, in its entirety or in part, has a color which varies along the visual indication.

In such embodiments, the visual indication may have different colors in different portions of the section of the film visible through the lens. An advantage with this solution is that it may be easier for the driver to distinguish the visual indication from the surrounding environment in the field-of-view, even if surrounding environment in the field-of-view comprise many different colors.

The varying color may also vary in such a way that the color at the start of the visual indication is different from the color at the end of the visual indication. Thus, the color of the visual indication may be related to the amount of film left in the supply magazine. Given only as an example, the color of the visual indication may be green when first appearing in front of the lens, but then change, gradually or stepwise, to red as the end of the film on the film roll is approaching. This may provide the driver with not only a single warning that the end of the film is approaching, but also information about if the end of the film is critically close, or if there is still some film on the roll for cleaning the lens a few more times.

In some embodiments, the visual indication is applied onto a surface of the transparent film.

In the present disclosure, the term "applied onto a surface" refers to any type of application on a surface. By way of example, the application may involve one or more separate physical entities fastened onto the surface of the film. Physical entities may be fastened by, but not limited to, an adhesive. Given as a second example, application of the visual indication onto the surface may involve any type of surface treatment of the film. Surface treatment may involve, but is not limited to, etching, embossing, heating, or chemical treatment of the film surface.

In some embodiments, the visual indication extends to the upper film edge.

In some embodiments, the visual indication extends over the upper film edge such that an edge part of the visual indication is visible when the film roll is observed from a top side of the film roll.

A special advantage of this solution is that, although the visual indication is only present on the trailing part of the film wound on the spindle and thus not visible on the leading end of the film, with the visual indication extending over the upper film edge it can still be seen when observing the top side of the initially full film roll. The user installing a full film roll in the supply magazine will thereby be able to easily distinguish film rolls having visual indication from standard film rolls without visual indication. By the present arrangement, one can make sure to install a film roll with visual indication into the supply magazine before a race.

Another advantage with this embodiment is that it allows the user to check also used film rolls to see if there is still a lot of film on the roll before reaching the film part with the visual indication. This will help in deciding whether a used film roll can be used again. In this manner it may be avoided that useful film rolls are thrown away, and may consequently lower the negative impact on the global environment.

In some embodiments, the transparent main film part has a height of at least 65% of the total film height between the upper film edge and an opposite bottom film edge. Under this arrangement, it will be appreciated, the height of the visual indication cannot exceed 35% of the total film height, and is confined to the upper 35% of the total film height.

Given as a non-limiting example, the total height of a film may be in the range of 30 mm to 40 mm, such as e.g. 32 mm or 39 mm. The visual indication may be up to 15 mm in height, such as 5 to 10 mm.

An advantage of this solution is that the visual indication is limited to an upper part of the film and does not extend down to the middle or bottom of the film. The middle and bottom parts of the film is through which the driver has the primary field-of-view. By the present arrangement, a film roll with a visual indication not interfering with the primary field-of-view of the driver may be achieved.

Some embodiments of eye protective goggles comprising an inventive film roll may further comprise a protective flap which is arranged on the front surface of the lens and which covers an upper portion of the transparent film along the upper film edge, wherein said visual indication, when having been advanced to the front surface of the lens to be visible to a user wearing the goggles, comprises at least one uncovered visual indication portion which is not covered by the protective flap and is visible to the user below a bottom edge of the protective flap.

The protective flap may be transparent in order to let light through to a translucent visual indication. However, when exposed to mud or dirt, light will no longer be allowed through the transparent protective flap. If the visual indication is only present in the area covered by the protective flap, the translucency of the visual indication can be impossible or very hard to utilize. An advantage of the solution of having at least one uncovered visual indication portion which is not covered by the protective flap and is visible to the user below a bottom edge of the protective flap, is that after having advanced the film to remove the dirty film and replacing it with new film, the translucent visual indication will be properly visible below the bottom edge of the protective flap even if the protective flap is still dirty and optically blocked.

In some embodiments of eye protective goggles comprising a protective flap, the visual indication, when having been advanced to the front surface of the lens to be visible by a user wearing the googles, comprises at least one covered visual indication portion which is covered by the protective flap. In the present embodiments, the visual indication may also comprise another visual indication portion which is not covered by the protective flap. Alternatively, the embodiments may comprise a visual indication that is fully covered in the vertical direction by the protective flap.

The different embodiments have largely been described above as separate embodiments. However, two or more of the above described embodiments may be combined. Given as a non-limiting example, the visual indication may be a translucent, dashed line with different colors in different segments.

BRIEF DESCRIPTION OF THE DRAWINGS

The inventive concept, some non-limiting preferred embodiments, and further advantages of the inventive concept will now be described with reference to the drawings in which:

FIG. 1CA is a front elevational view of the prior art goggles and film advance system of FIG. 1B.

FIG. 1CB is a cross-sectional bottom view of the film advance system shown in FIG. 1CA.

FIG. 2A is a front elevational view of the prior art goggles and film advance system shown in FIG. 1A, with the film advance system in a first condition during a sequence of use.

FIG. 2B is a front elevational view of the prior art goggles and film advance system shown in FIG. 1A, with the film advance system in a second condition during a sequence of use.

FIG. 2C is a front elevational view of the prior art goggles and film advance system shown in FIG. 1A, with the film advance system in a third condition during a sequence of use.

FIG. 4AB is a cross-sectional bottom view of the film advance system shown in FIG. 4AA.

FIG. 4BB is a cross-sectional bottom view of the film advance system shown in FIG. 4BA.

FIG. 4CB is a cross-sectional bottom view of the film advance system shown in FIG. 4CA.

FIG. 4DB is a cross-sectional bottom view of the film advance system shown in FIG. 4DA.

DETAILED DESCRIPTION OF THE PREFERRED EMBODIMENTS

Prior Art

Figure 1A:
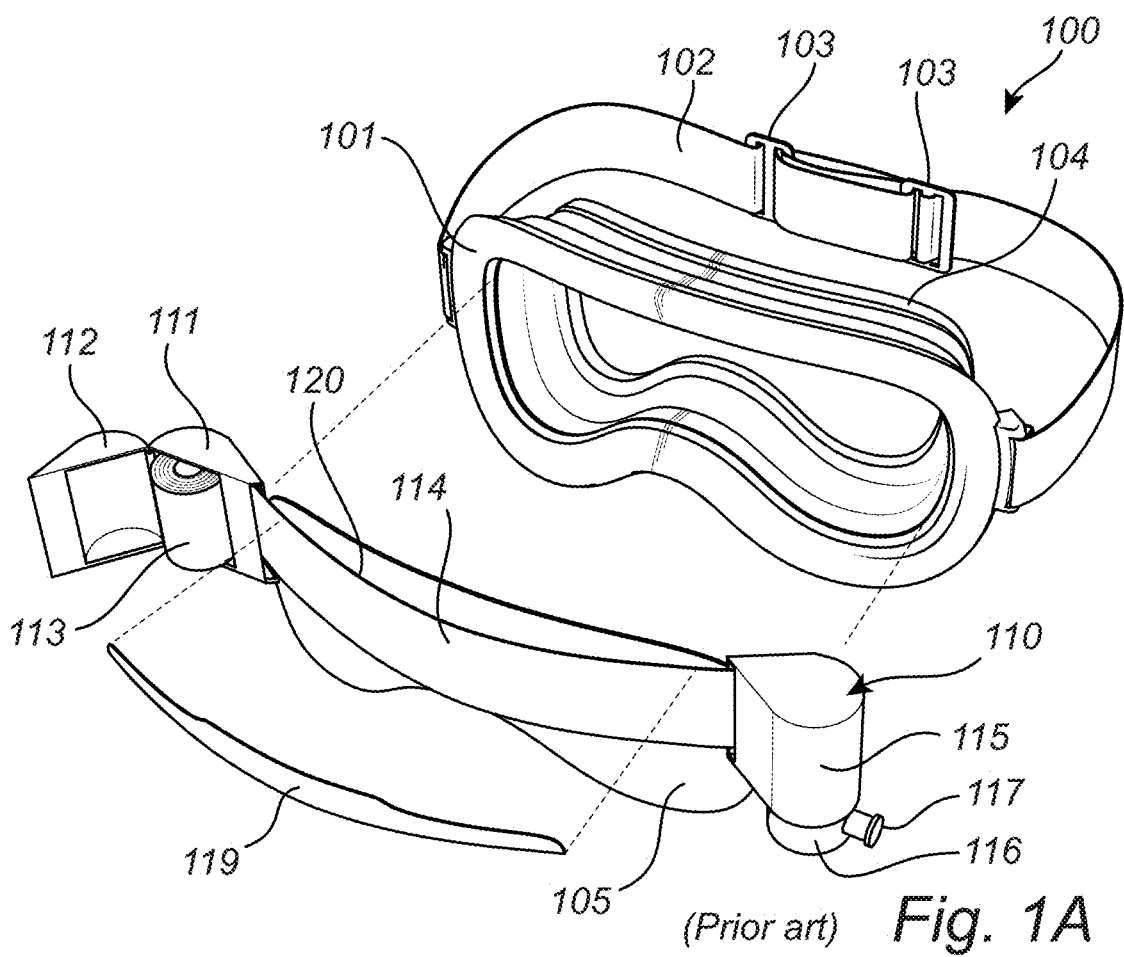
FIG. 1A is a perspective view of an exemplary set of prior-art goggles in conjunction with a prior art film advance system which is shown removed from, but attachable to, the goggles.
Figure 1B:
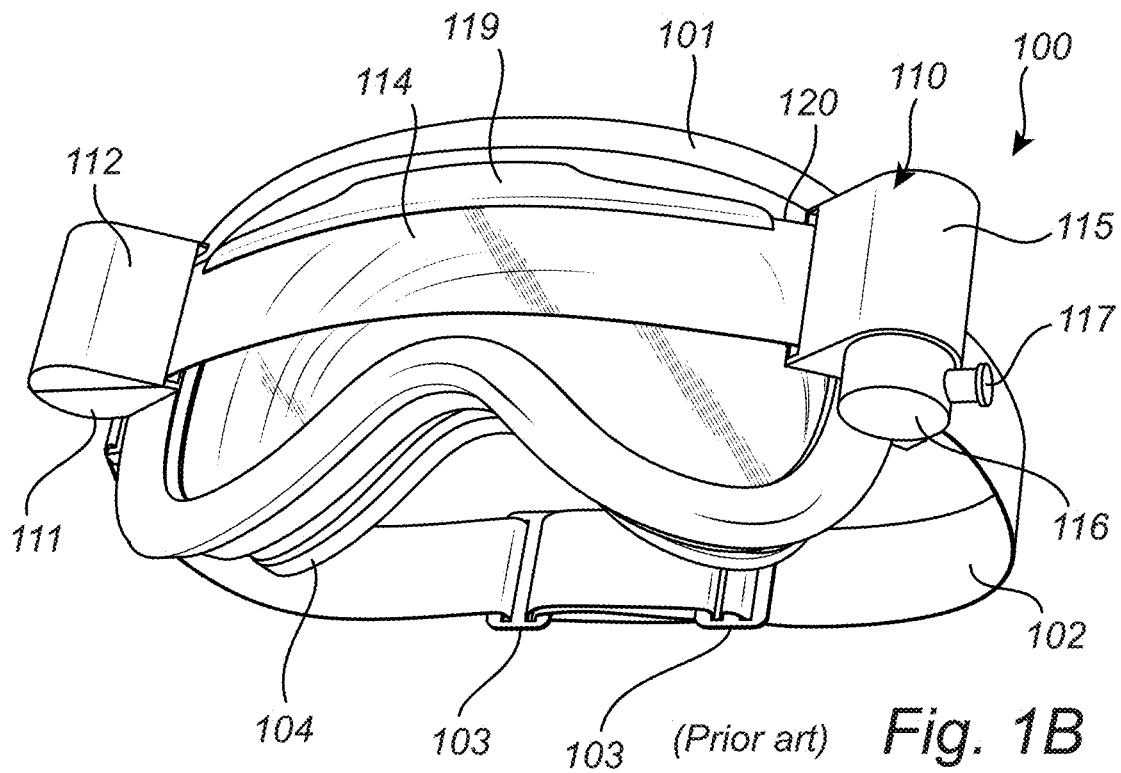
FIG. 1B is a perspective view of the prior art goggles shown in FIG. 1A, attached to the prior art film advance system shown in FIG. 1A.

FIGS. 1A and 1B illustrate an example of a set of prior-art goggles 100 with a film advance system 110. FIG. 1A illustrates a partly disassembled set of goggles 100 and film advance system 110, whereas FIG. 1B illustrates the same set of goggles 100 and film advance system 110 fully assembled. The goggles 100 comprise a goggle frame 101 which is supplied with an elastic strap 102 connected to two lateral sides of the frame 101. When the goggles 100 are in use, the frame 101 can be placed on the driver's face around the eyes and the elastic strap 102, functioning as a headband, can be wrapped around the back of the driver's head, keeping the frame 101 steadily in place in front of the eyes. The elastic strap 102 is equipped with buckles 103 allowing adjustment of the elastic strap 102 length, in order to fit different drivers. The frame 101 is also equipped with padding 104 on the edge facing the driver, for a more comfortable fit of the goggles 100 to the face.

The frame 101 is designed to fit a lens 105 of a sturdy, transparent material. FIG. 1A illustrates the lens 105 prior to being mounted in the frame 101, whereas FIG. 1B illustrates the lens 105 mounted in the frame 101. The lens 105 may be made of, but is not limited to, plastic or glass. The lens 105 is equipped with a film advance system 110. The film advance system 110 comprises film supply magazine 111, which in this embodiment is arranged on the right side of the lens 105, as seen from the driver's perspective. The supply magazine 111 has an openable hatch 112. When the hatch 112 is open, access to the inside of the supply magazine is provided, allowing a film roll 113 of a flexible, transparent film 114 to be inserted into the supply magazine 111. In the center of the film roll 113 is a supply spindle (not shown) onto which the transparent film is wound. When the film roll 113 has been inserted into the supply magazine 111, the spindle functions as a rotational axle around which the film roll 113 can rotate freely inside the supply magazine 111.

The film advance system 110 further comprises a film take-up magazine 115, which is arranged on the left side of the lens 105, as seen from the driver's perspective. The transparent film 114 on the film roll 113 is installed into the film advance system 110 such that the transparent film 114 extends across the lens 105 from the supply magazine 111 to the take-up magazine 115. Inside the take-up magazine is a take-up spindle 122 (see FIG. 1CB) onto which the leading end of the transparent film 114 is wound. The spindle from a previously used and emptied film roll is normally used as the take-up spindle for the subsequent film roll.

The take-up spindle and magazine 115 are connected to a film advance mechanism 116 arranged to enable the transparent film 114 to be advanced across the lens 105 in the direction from the supply magazine 111 to the take-up magazine 115. The film advance mechanism 116 is activated by the driver manually pulling a knob 117 at the end of a flexible cord connected to a mechanical actuator, winding a used film section into the take-up magazine 115.

The film advance system 110 in FIGS. 1A and 1B includes a protective flap 119 to prevent water, mud or dirt from entering between the lens 105 and the transparent film 114. The protective flap 119 presents an upper portion having an adhesive inner surface for attaching the protective flap on the lens 105. The protective flap 119 is positioned such that the protective flap 119 is fastened on the lens 105 alongside the upper edge 120 of the transparent film 114. A lower, preferably transparent portion of the protective flap 119 covers the upper edge 120 of the transparent film 114 and allows the transparent film 114 to move behind the protective flap 119.

FIGS. 1CA, 1CB illustrates a front view of the goggles 100, along with a cross-sectional bottom view of the film advance system 110. As shown in the cross-sectional bottom view, the supply magazine 111 contains an essentially full film roll 113 on the supply spindle 121. The transparent film 114 extends from the supply magazine 111 to the take-up magazine 115. The leading end of the transparent film 114 is wound onto the take-up spindle 122, and the take-up magazine is essentially empty of film. Reference numeral 123 indicates the length of the section of the film 114 visible through the lens 105, which may be equal to the length of the film section extending from the supply magazine 111 to the take-up magazine 115.

FIGS. 2A to 2C illustrate three steps in the sequence of cleaning the field-of-view using a film advance system 110 on a set of goggles 100. FIG. 2A illustrates a dirty set of goggles 100, where the dark sections represent mud 130 present on the transparent film 114, on the lens 105 outside the transparent film 114, and on the protective flap 119.

FIG. 2B illustrates the knob 117 at the end of the flexible cord 118 being pulled. As the flexible cord 118 is connected to the mechanical actuator of the film advance mechanism 116, the transparent film 114 is advanced across the lens 105 by winding the dirty film section into the take-up magazine 115 and onto the take-up spindle 122. Thereby, a new clean transparent film section is being pulled off of the film roll 113, out of the supply magazine 111, and onto the lens 105. In FIG. 2B, the film 114 has been advanced approximately half of the length 123 of the visible section of the film. Accordingly, the section of the of film 114 closest to the supply magazine 111 is a clean film section, whereas the film section closest to the take-up magazine 115 contains mud stains 130.

In FIG. 2C, the film advancement has been completed and the flexible cord 118 has been retracted into the film advance mechanism 116 by a spring mechanism (not shown). The film has been advanced at least the length 123 of the visible section of the film 114, such that the dirty section of the film 114 shown in FIGS. 2A and 2B has now been replaced by a clean section of film 114 from the film roll 113 in the supply magazine 111. As illustrated in FIG. 2C, only the part of the lens 105 covered by the film 114 is "cleaned", restoring the clear field-of-view through the clean film 114. Parts of the lens 105 not covered by the film 114, e.g. the lower lens parts, still contain mud stains 130. It should be noted that the field-of-view is not cleared over the area where the upper edge portion of the transparent film 114 is covered by the protective flap 119, as the mud stains 130 are located on the outer surface of the protective flap 119 and not on the film 114 in this area.

Embodiments of the Inventive Concept

In the embodiments of the inventive concept described below, the structure and function of the googles and the film advance system will not be repeated. The same structure and function applies to all the disclosed embodiments, and the same reference numerals are used in general.

Figure 3A:
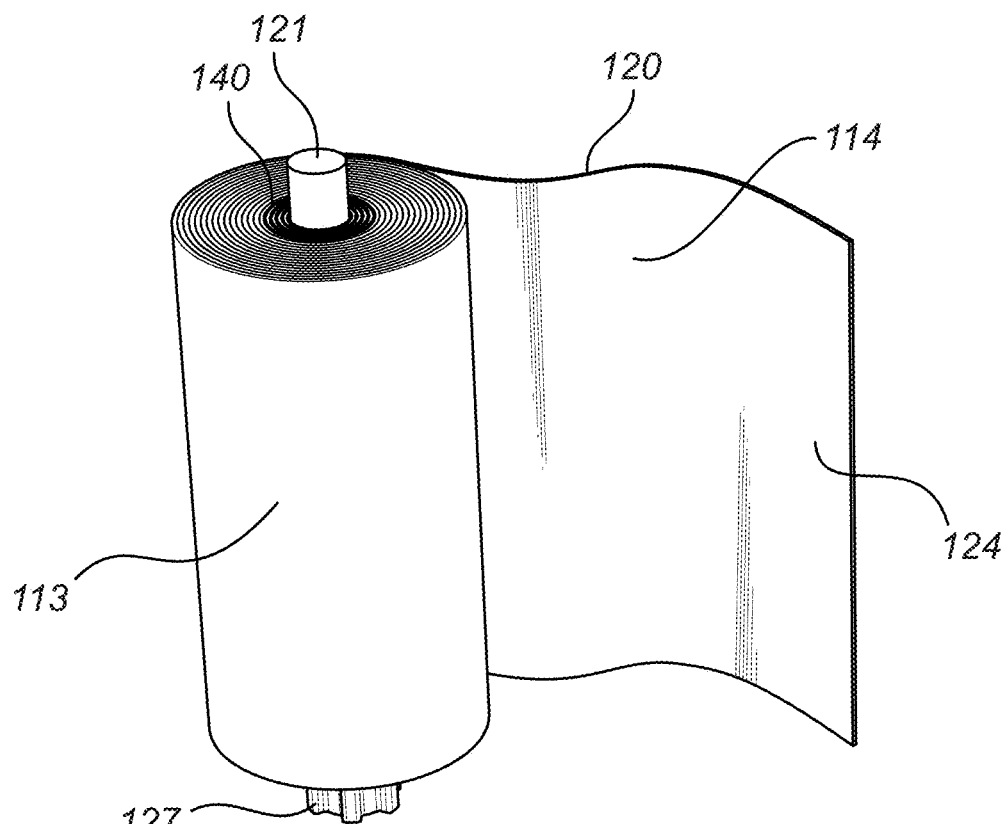
FIG. 3A is a perspective view of a film roll shown in rolled condition having features of the invention.

FIG. 3A illustrates a film roll 113 according to a first embodiment of the inventive concept. A transparent film 114 is in the form of a rectangular strip. The transparent film is wound onto a supply spindle 121, such that only a leading end 124 of the film 114 may be freely extended, whereas the trailing end 126 is in contact with, and optionally releasably adhered to the supply spindle 121.

Figure 3B:
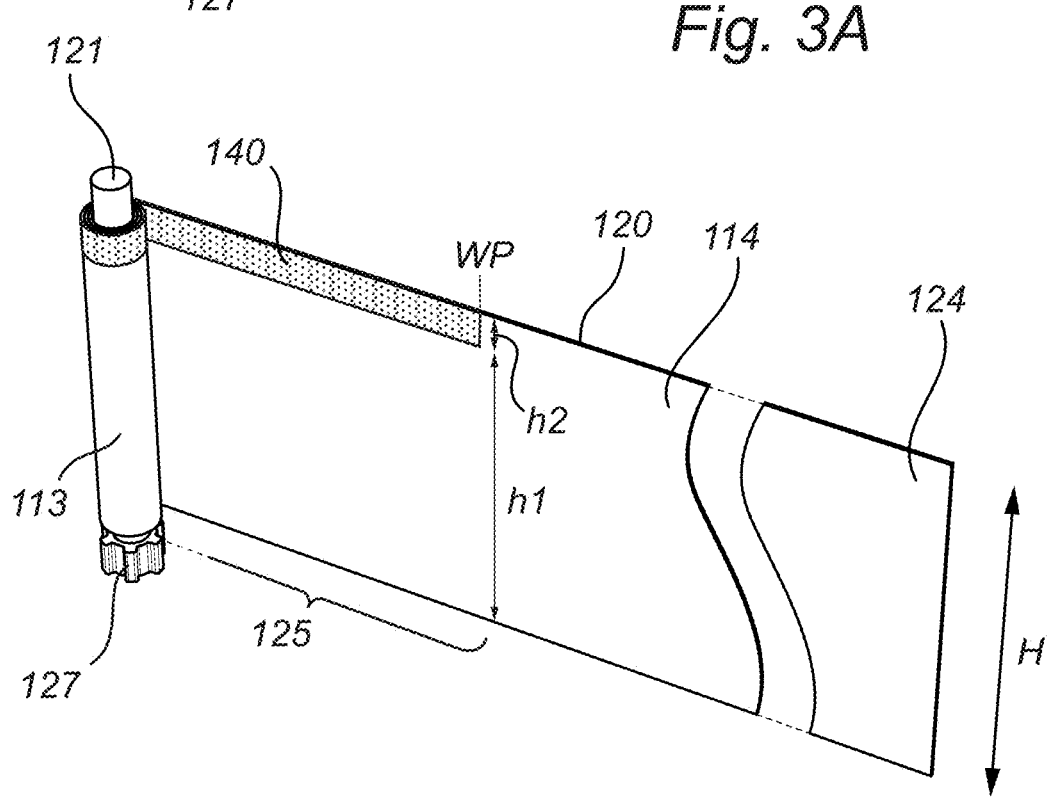
FIG. 3B is a perspective view of the film roll in FIG. 3A, shown in a partially unrolled condition.

As shown in FIG. 3B, the transparent film 114 is provided with a visual indication 140 at the upper edge 120 of the film 114. The visual indication 140 is only present on, i.e. limited to, a trailing part of the film 114, and is therefore not visible on the free, leading film end 124 shown in FIG. 3A. In this embodiment, the visual indication 140 extends up to and over the upper edge 120 of the film 114, such that an edge part of the visual indication 140 is visible when the film roll 113 is observed from a top side of the film roll 113. In alternative embodiments, this effect may be accomplished also by the edge indication being a separate indication, not in connection with or an extension of the visual indication 140, while still being visible on the top side of the film roll 113.

In order to fit and connect the film roll 113 to a film advance system 110 (see FIGS. 4AA, 4AB), the ends of the supply spindle 121 are adapted for connection to such a system. In the present embodiment, the bottom end of the supply spindle has been equipped with cogs or splines 127 for this purpose. However, in other embodiments the adaption may be different, such as a slit across the end of the supply spindle 121.

FIG. 3B illustrates the film roll 113 of the embodiment described in FIG. 3A, where a major part of the film 114 has been extended such that the visual indication 140 starts to appear. At the longitudinal position denoted WP (Warning Position), the visual indication 140 begins. In this embodiment, the visual indication 140 extends in the longitudinal direction to the trailing part 125 of the film 114. When in use together with goggles 100 with a film advance system 110, the warning position WP at which the visual indication 140 starts, will provide the driver with a visual warning that a limited number of clean film sections remain in the film roll 113 in the supply magazine 111. This visual warning will allow the driver to plan the use of the remaining film length for the remaining part of the race, in order to avoid running out of film before finishing the race. As a non-limiting example, the warning position WP may be selected such that 10 to 15 clean film sections remain in the supply magazine 111. As another example, the warning position WP may be selected such that 10% to 20% of the total film length remain in the supply magazine 111. Preferably a minimum number of clean film section should remain, such as at least 5 to 20, preferably at least 10.

The film 140 has a total film height H, and a transparent main film part below the visual indication 140 having a height h1. The height of the visual indication 140 is denoted h2 (equal to H−h1). In the present embodiment, the height h2 of the visual indication 140 is significantly smaller than H and h1, such that the visual indication 140 does not extend down from the upper edge 120 into and disturb a primary field-of-view of the driver. By the present arrangement, a visual warning visible to the driver without disturbing the driver's primary field-of-view may be provided.

Figure 4A:
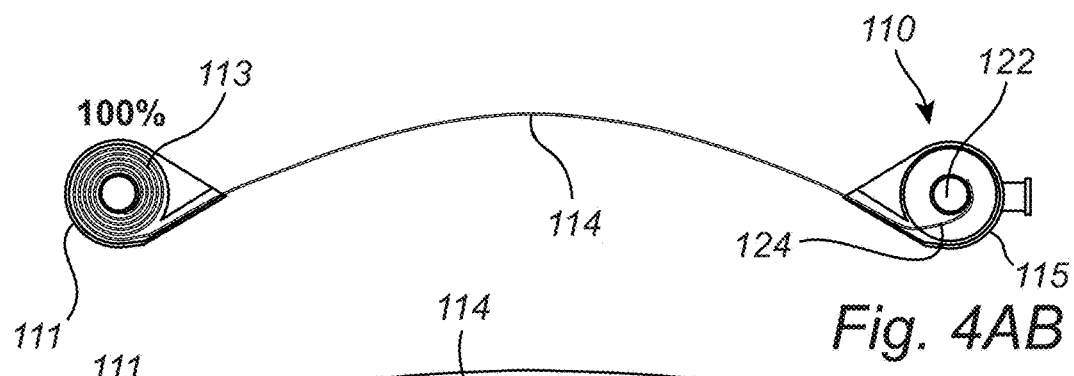
FIG. 4AA is a front elevational view of a film advance system attached to goggles, the film advance system being in a first condition, in which features of the invention are shown.
Figure 4A:
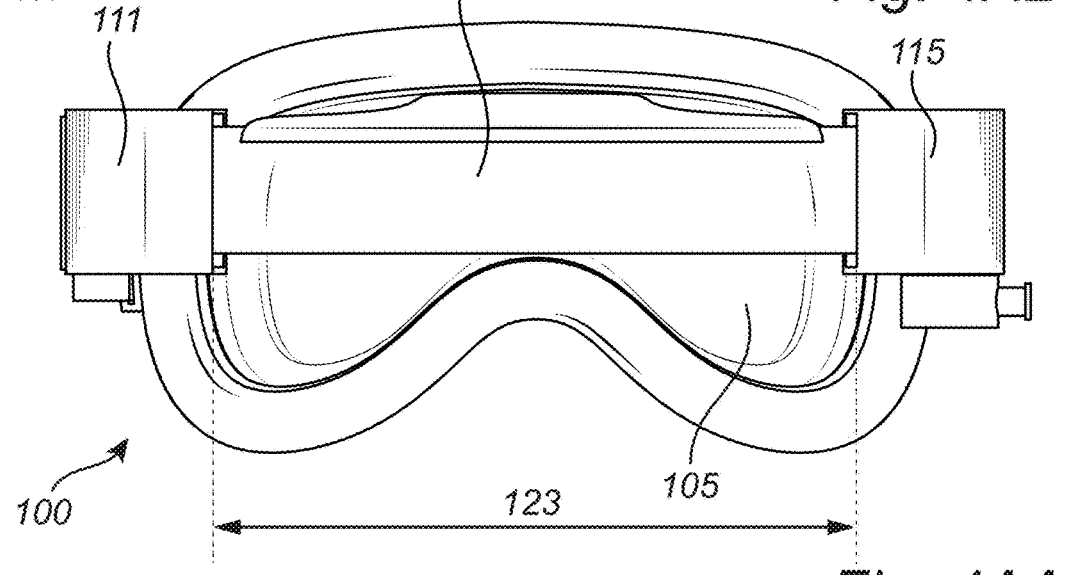

FIG. 4AA, illustrates a set of goggles 100 including a film advance system 110 and a film roll 113 according to the first embodiment shown in FIGS. 3A and 3B. As mentioned above, the goggles 100 with the film advance system 110 described here and onwards may present features and functions from the prior-art in FIG. 1 and FIG. 2 described above, the details of which will not be repeated here.

Figure 4B:
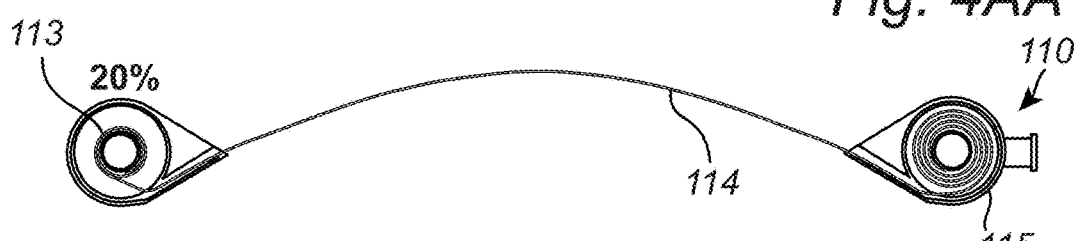
FIG. 4BA is a front elevational view of a film advance system attached to goggles, the film advance system being in a second condition, in which features of the invention are shown.
Figure 4B:
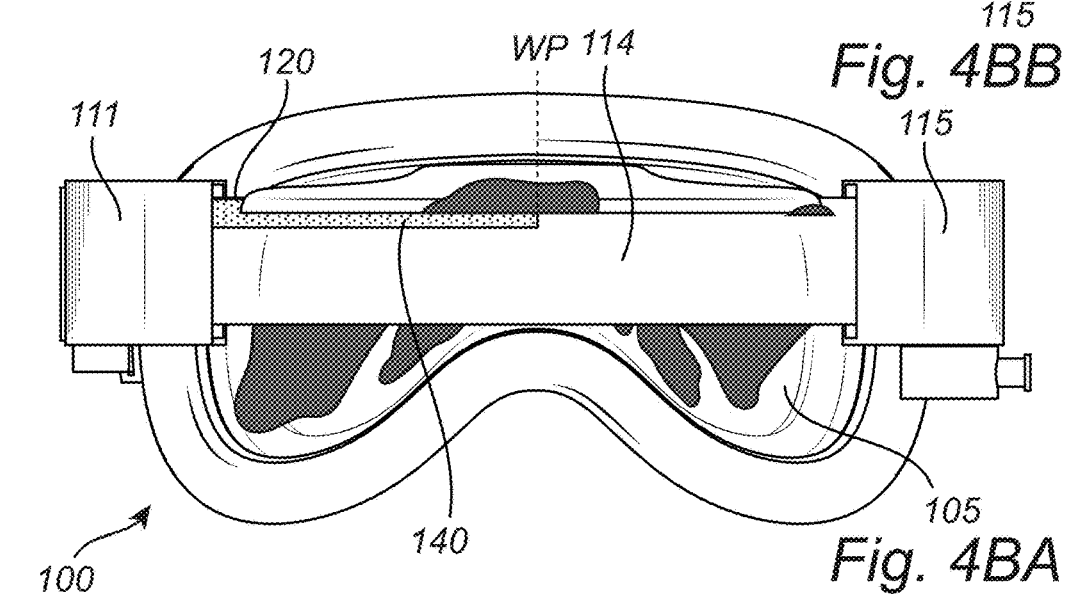
Figure 4C:
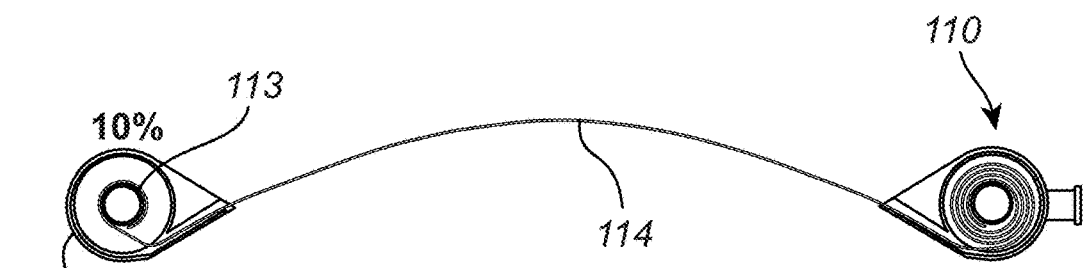
FIG. 4CA is a front elevational view of a film advance system attached to goggles, the film advance system being in a third condition, in which features of the invention are shown.
Figure 4C:
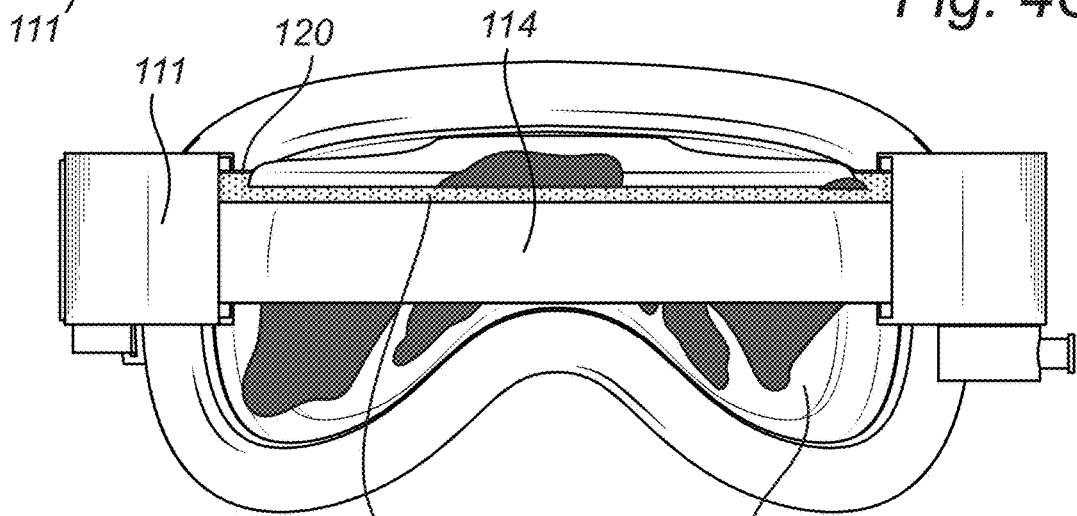
Figure 4D:
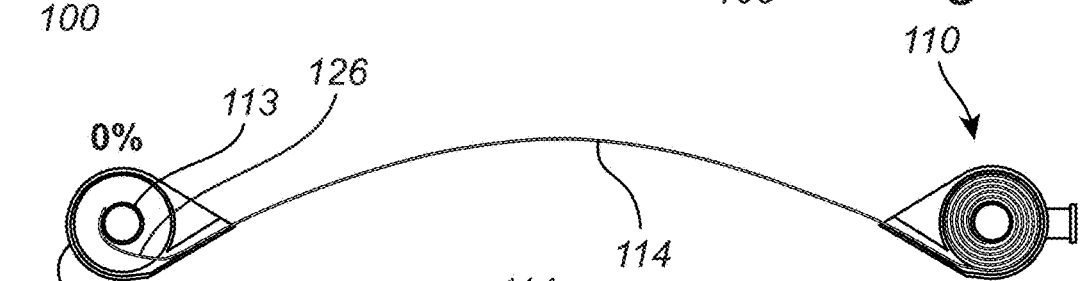
FIG. 4DA is a front elevational view of a film advance system attached to goggles, the film advance system being in a fourth condition, in which features of the invention are shown.
Figure 4D:
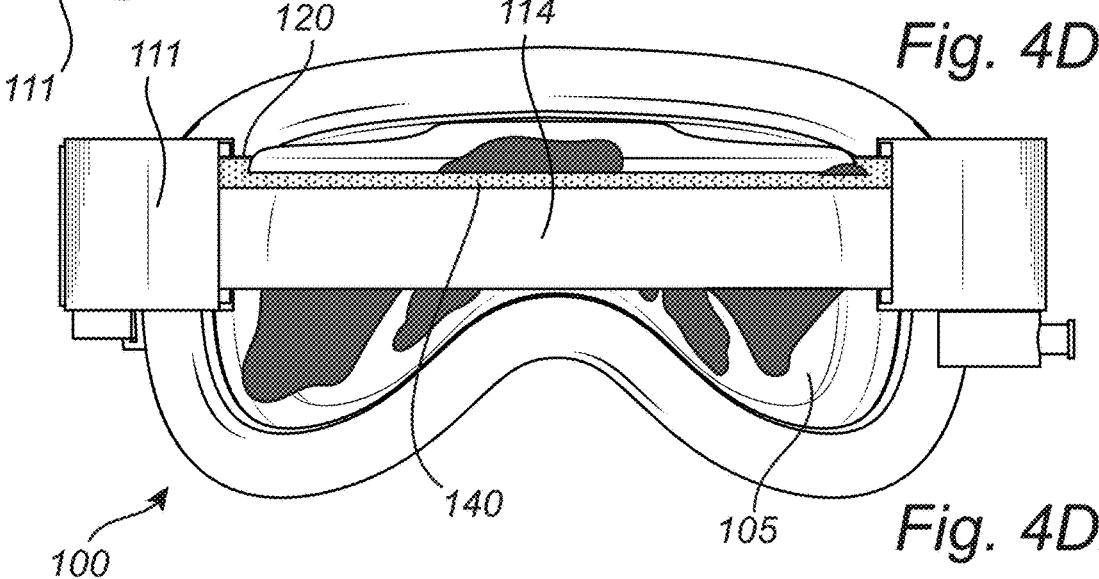

FIGS. 4AA to 4DB illustrate four stages of an embodiment of the inventive concept, when in use, from a full film roll (FIGS. 4AA, 4AB) to an empty film roll 113 (FIGS. 4DA, 4DB). FIG. 4AA illustrates a set of goggles 100 with a film advance system 110, along with a cross-sectional bottom view of the film advance system 110. In FIG. 4AA, a full film roll 113 has been installed in the supply magazine 111, with the transparent film 114 extending across the lens 105 from the supply magazine 111 into the take-up magazine 115 where the leading film end 124 of the film 114 is wound onto the take-up spindle 122. At this stage, essentially 100% of the transparent film 114 on the film roll 113 is still in the supply magazine 111, apart from the first section of film extending across the lens 105 and into the take-up magazine 115.

FIGS. 4BA, 4BB illustrates a subsequent stage appearing after a certain part of a race, where the visual indication 140 on the film 114 appears in front of the lens 105 for the first time. This will occur after the film 114 has been advanced by the driver a number of times across the lens 105 using the film advance mechanism. The visual indication 140 starts at warning position WP, and extends along the upper edge 120 of the film 114 into the supply magazine 111. The visual indication 140, or warning marking, will create a visual contrast compared to the previous part of the film 114 seen by the driver through the lens 105, and will provide the driver with a visual warning that the supply magazine 111 will be running out of film 114 in a limited number of film advancements.

In the present embodiment, shown as an illustrative and non-limiting example only, the visual warning occurs when 20% of the original amount of film 114 remains in the supply magazine 111. By way of example, this may correspond to having enough film 114 in the supply magazine 111 for about 10 to 15 more full film advancements before all film 114 in the supply magazine 111 is spent. In other words, the length of transparent film 114 remaining in the supply magazine 111 may correspond to 10 to 15 remaining clean film sections, where each section has a length 123 corresponding to the width of the lens 105 of the goggles 100.

FIGS. 4CA, 4CB illustrates a subsequent stage at which only 10% of the original film roll 113 remains in the supply magazine 111. The visual indication 140 is still present and visible on the section of the film 114 in front of the lens 105. The presence of the visual indication 140 provides a reminder to the driver that the supply magazine 111 will be running out of film 114 in a few more film advancements.

FIGS. 4DA, 4DB illustrates a final stage at which 0% of the original film roll 113 is left in the supply magazine 111, thus the end of the film 114 in the supply magazine 111 has been reached. The visual indication 140 on the transparent film 114 is still visible on the section of film 114 in front of the lens 105, thus the visual indication 140 extends from the position WP, as shown in FIGS. 4BA, 4BB, along the upper edge 120 of the film 114 and all the way to the trailing end 126 of the film 114. Hence the warning to the driver is maintained all the way to the end of the film 114.

It is also conceivable that the visual indication starts at WP and extends towards the end of the film 114, but does not extend to the very end of the film 114, e.g. the short film end which cannot be pulled over the lens may lack visual indication 140.

Figure 5A:
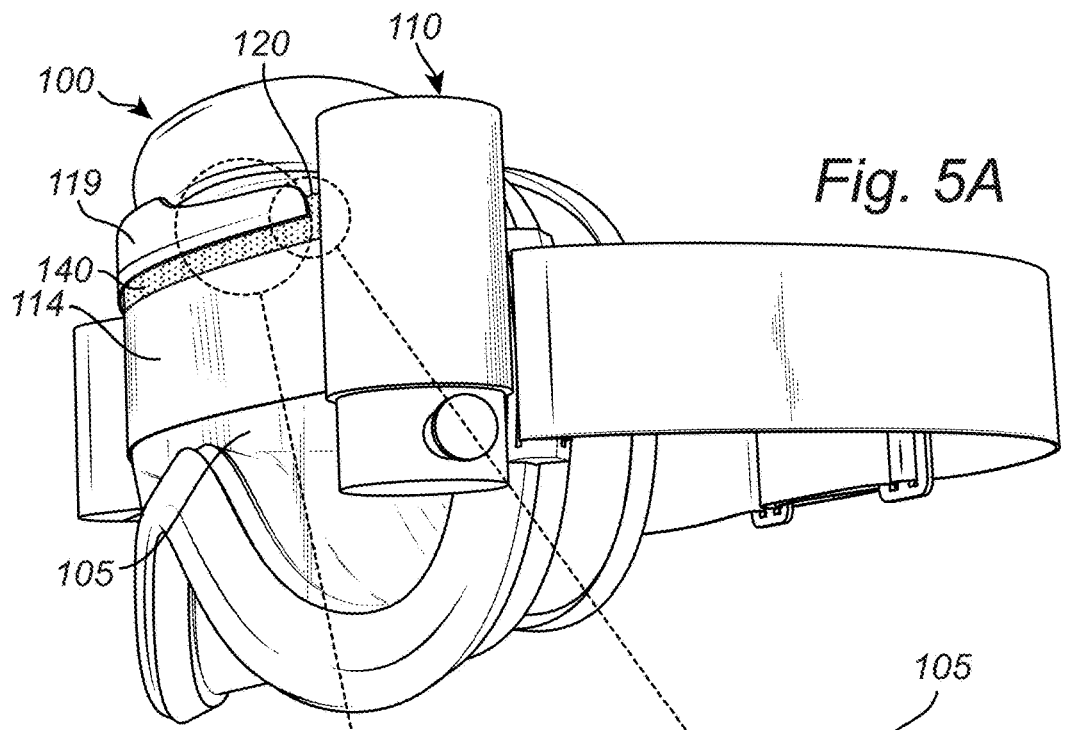
FIG. 5A is a perspective view of a set of goggles provided with a film advance system according to an embodiment of the invention.

As shown in FIG. 5A, the set of goggles 100 in FIGS. 4AA to 4DA is provided with a protective flap 119, as described in the prior-art. The upper part of the protective flap 119 is attached to the lens 105 on the area just above the upper edge 120 of the film 114. The upper part of the protective flap 119 may typically be provided with an adhesive film on its inner side. The lower part of the protective flap 119 which is not attached to the lens 105, extends downwards to at least partly cover an upper portion of the transparent film 114, thereby providing the intended function of the protective flap 119. In the present embodiment, the lower part of the protective flap 119 covering the upper portion of the film 114, is transparent. Typically, the upper part of the protective flap 119 attached to the lens 105 may be non-transparent, and may instead be used to block sunlight. As described above, the purpose of the protective flap 119 covering the upper portion of the transparent film 114 is to prevent e.g. water, mud or dirt from entering between the lens 105 and the transparent film 114.

In the present embodiment, the position and the height h2 of the visual indication 140 is selected such that the visual indication 140 is only partly covered in the height direction by the transparent lower part of the protective flap 119. Since the lower part of the protective flap 119 is transparent, light may pass through the protective flap 119 and onto the visual indication 140. With a translucent visual indication 140, the light is subsequently allowed to pass through the visual indication 140 and reaching the eyes of the driver. The cross-sectional view FIG. 5B illustrates in greater detail how the upper non-transparent part of the protective flap 119 is attached to the outer surface of the lens 105, and how the lower transparent part of the protective flap 119 extends downwards to cover the upper portion of the transparent film 114.

Figure 5C:
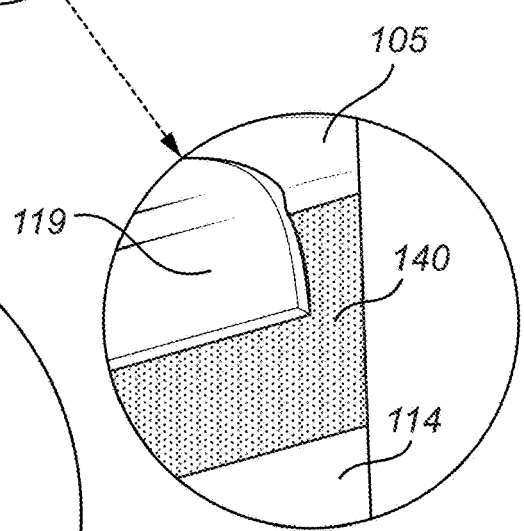
FIG. 5C is a detail view of a portion of FIG. 5A which is identified in FIG. 5A by a circle with an arrow to FIG. 5C and shows a visual indication in a first location in relation to a protective flap.
Figure 5B:
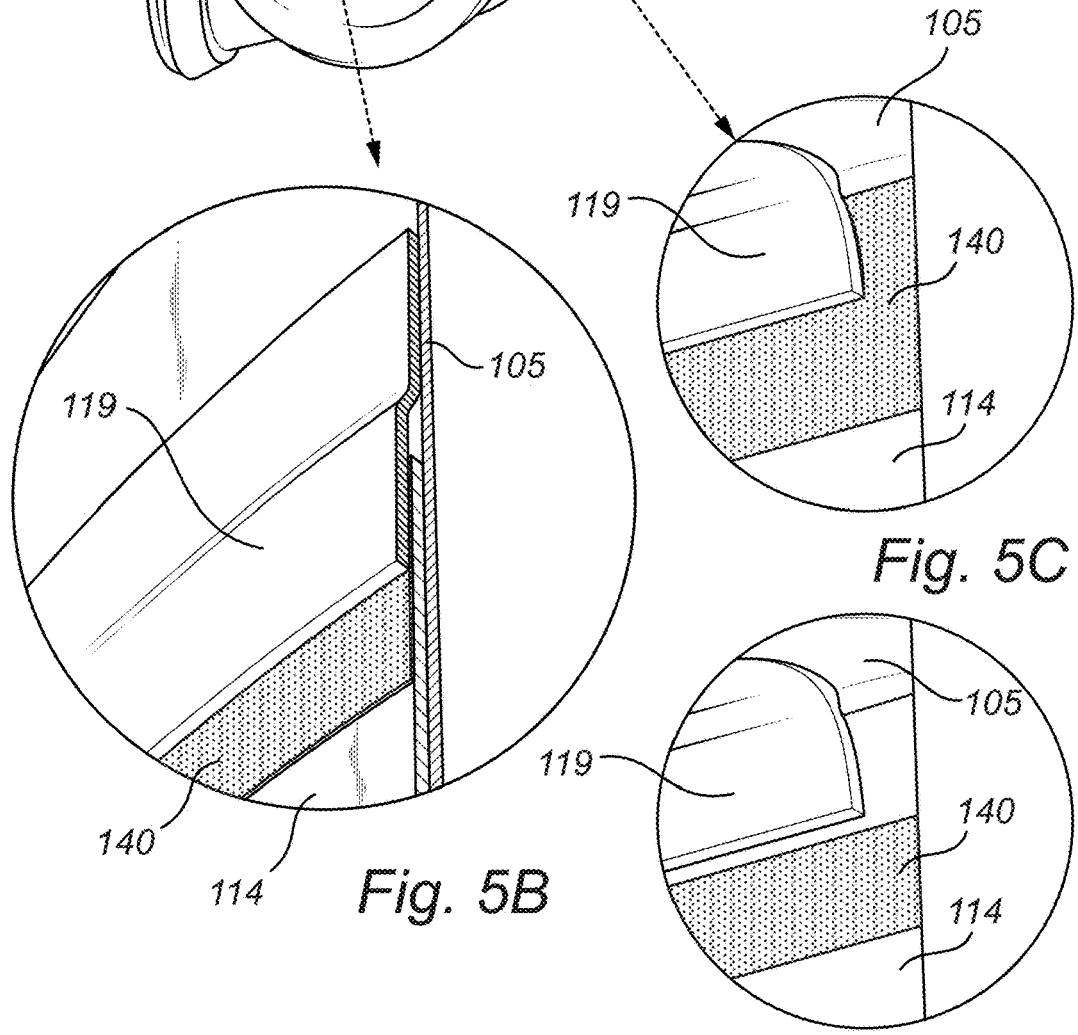
FIG. 5B is a detail view of a portion of FIG. 5A which is identified in FIG. 5A by a circle with an arrow to FIG. 5B.

FIG. 5C shows an alternative view of the same features at shown in FIGS. 5A and 5B, and illustrates how the full height h2 of the visual indication may be visible on the right and left sides of the protective flap 119.

Figure 5D:
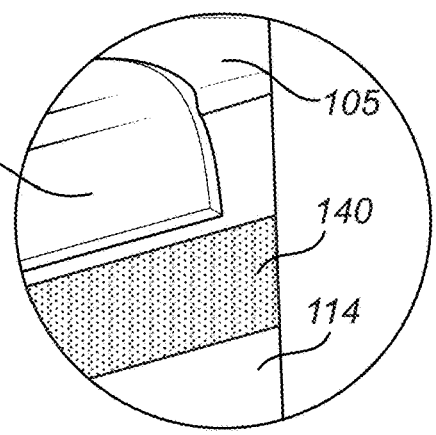
FIG. 5D is a detail view of the same portion of FIG. 5A as shown in FIG. 5C and shows a visual indication in a second location in relation to a protective flap.

FIG. 5D illustrates an alternative embodiment, in which the visual indication 140 may be arranged only on a portion of the transparent film 114 not covered by the protective flap 119.

According to another alternative embodiment, the visual indication 140 may be arranged only on an upper portion of the transparent film 114 completely covered by the protective flap 119. However, the embodiments in FIGS. 5A to 5D are preferred. If the outer surface of the protective flap gets covered entirely or partly by mud, the mud may prevent light from passing through the transparent lower part of the protective flap 119. If the visual indication 140 is only present in the area covered by the flap, it may in certain situations be more difficult for the driver to notice it. Especially, if the visual indication 140 is translucent, the translucency of the visual indication 140 may be hard to utilize. At least from this point of view, the embodiments in FIGS. 5A to 5C are advantageous.

Figure 6:
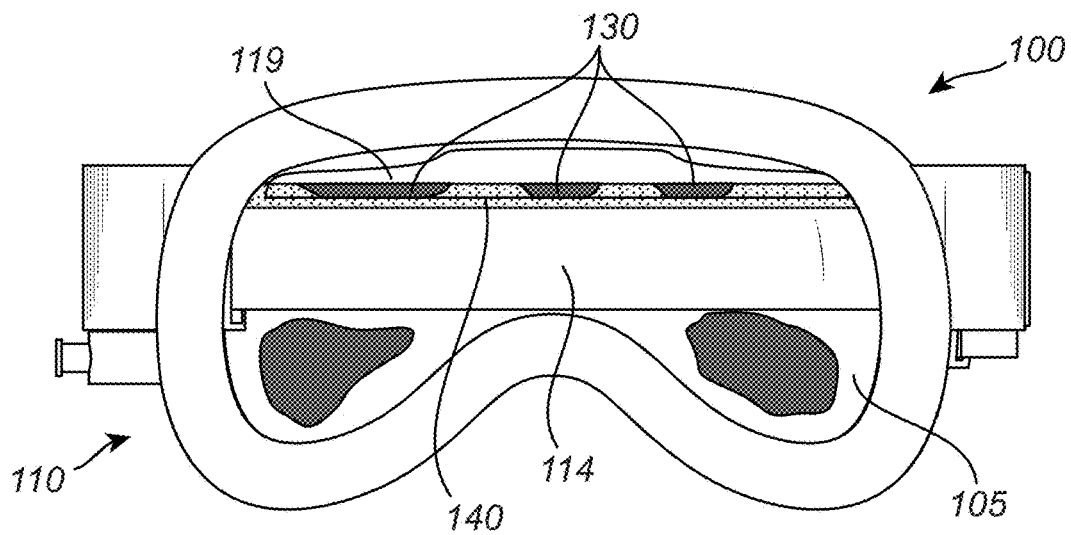
FIG. 6 is an exemplary outward view from inside the goggles of FIG. 4CA.

FIG. 6 illustrates the driver's view from inside the goggles 100 looking out through the lens 105. The visual indication 140 in this embodiment maybe the same as described above. FIG. 6 shows how mud stains 130 on the transparent lower part of the protective flap 119 prevent light from passing through, making it difficult for the driver to see the visual indication 140 covered by such mud stains 130 on the protective flap 119. FIG. 6 also shows that the lower part of the visual indication 140 not being covered by the protective flap 119 is easily seen when the film 114 has been advanced.

FIGS. 7 to 11 illustrate alternative embodiments of visual indications 140 on transparent film 114. It should be noted that these alternative embodiments only serve as examples, and the inventive concept is not in any way limited to these examples. The alternative embodiments in FIGS. 7 to 11 are merely schematics and are not drawn to scale. Therefore, the dimensions and proportions of the details in the drawings may differ from the corresponding dimensions and proportions on real films.

Figure 7:
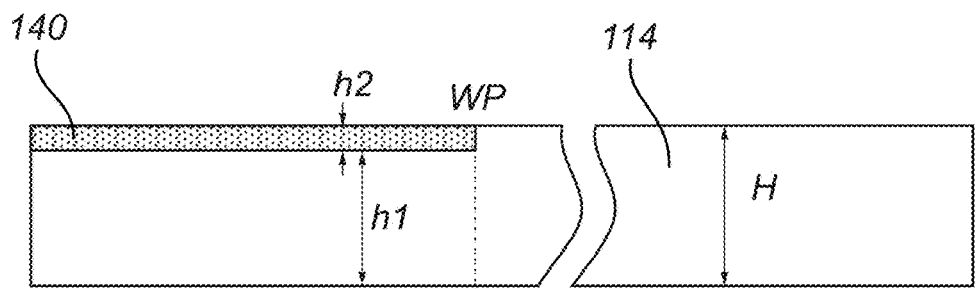
FIG. 7 is a front elevational view of an embodiment of a transparent film provided with a uniform visual indication.

FIG. 7 illustrates an embodiment having a uniform visual indication 140, essentially as shown in FIG. 3B, and FIGS. 4BA to 4DB. The visual indication 140 may be translucent. The visual indication 140 may have a suitable color, such as red, green, white, to provide an efficient visual warning effect, i.e. an easily detectable contrast indication. The visual indication 140 starts at the warning position WP, and extends uniformly to the trailing end of the film 114. In this embodiment, the visual indication 140 has a constant height. The amount of film 114 left in the supply magazine 111 when the warning position WP appears in front of the lens 105 may last for 10 to 15 full film advancements. As defined in previous figures, one full film advancement may correspond to advancing the film 114 across the lens 105 by the length 123 of the section of the film 114 visible through the lens 105. A full film roll may typically last for 50 full film advancements or more.

Figure 8:
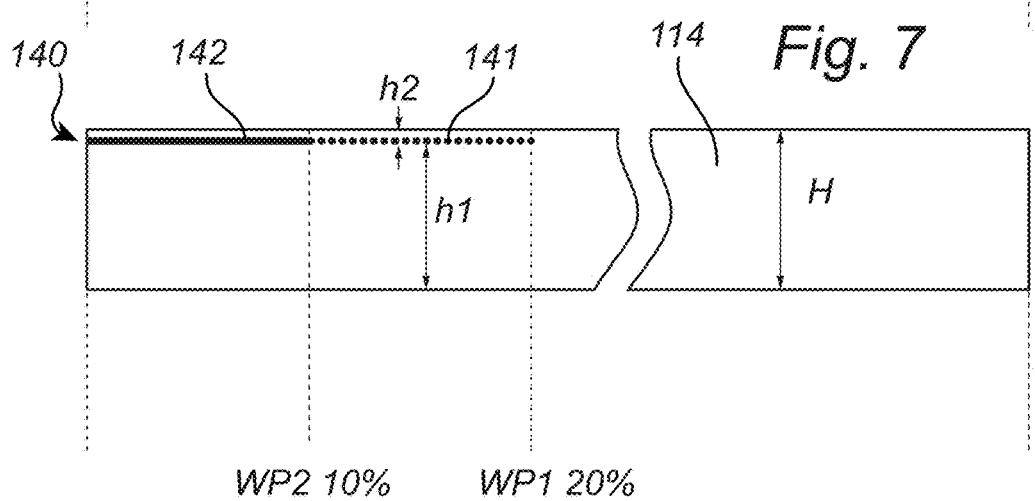
FIG. 8 is a front elevational view of an embodiment of a transparent film where the visual indication first appears as dots, and then as a continuous line.

FIG. 8 illustrates an embodiment of the transparent film 114 where the visual indication 140 appears at a first warning position, WP1, e.g. as dots 141, and e.g. as a continuous line 142 after a second warning position, WP2. This embodiment provides the driver with two distinct warnings. By way of example, when WP1 appears in front of the lens 105, the amount of film 114 left in the supply magazine 111 may last for essentially 15 full film advancements. When WP2 subsequently appears in front of the lens 105, the amount of film left in the supply magazine may last for essentially 8 full film advancements. In FIG. 8 the visual indication 140 is illustrated as solid non-translucent dots and a solid non-translucent line. Other embodiments including a dotted or dashed visual indication may have one warning position only, i.e. a dotted/dashed visual indication extending from a single warning position WP towards the trailing film end.

Figure 9:
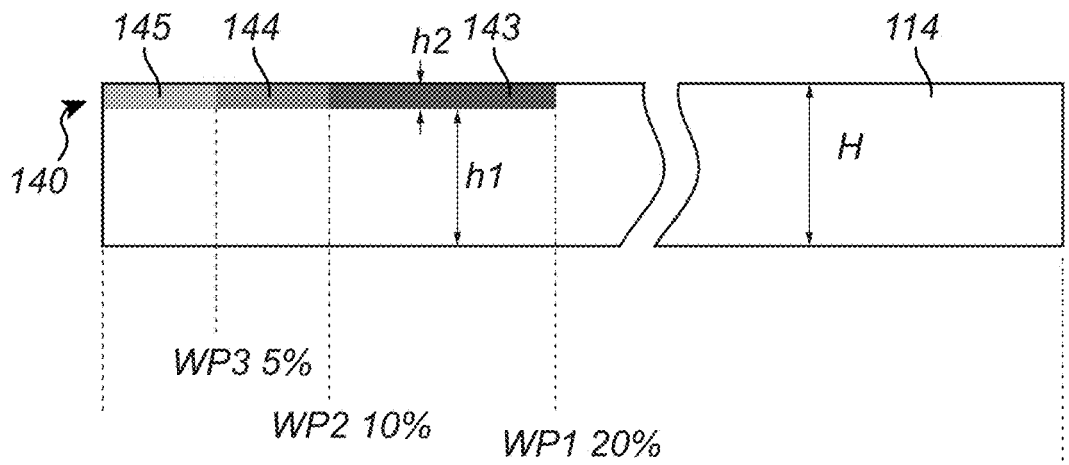
FIG. 9 is a front elevational view of an embodiment of a transparent film in which the visual indication has different colors in different sections.

FIG. 9 illustrates an embodiment of the transparent film 114 in which the visual indication 140 has a constant height h2, and different colors in different longitudinal sections. By way of example, between a first warning position, WP1, and a second warning position, WP2, the visual indication has a first color green 143. Between a second warning position, WP2, and a third warning position, WP3, the visual indication has a different second color yellow 144. Between a third warning position, WP3, and the end of the film roll 113, the visual indication 140 has the a still different third color red 145. This embodiment provides the driver with three distinct warnings. By way of example, when the first warning WP1 appears in front of the lens 105, the amount of film 114 left in the supply magazine 111 may last for essentially 15 full film advancements. When WP2 appears in front of the lens 105, the amount of film left in the supply magazine may last for essentially 8 full film advancements. When WP3 appears in front of the lens 105, the amount of film left in the supply magazine may last for essentially 4 full film advancements. In this embodiment, the colors may be different from the colors specified here. In a preferred embodiment, the colors are translucent, however, also non-translucent colors may be possible.

Figure 10:
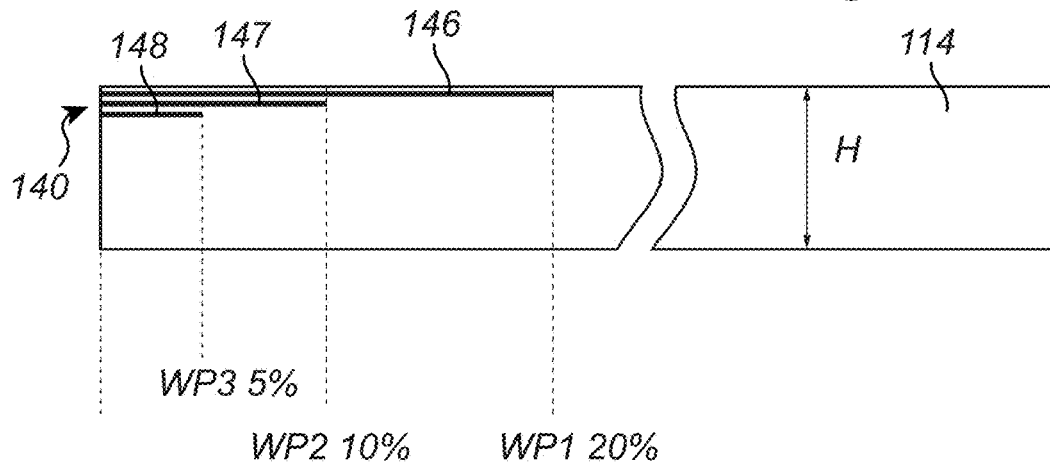
FIG. 10 is a front elevational view of an embodiment of a transparent film where the visual indication appears as an increasing number of lines.

FIG. 10 illustrates an embodiment of the transparent film 114 where the visual indication 140 appears as an increasing number of parallel lines. At a first warning position, WP1, one line 146 appears in front of the lens. At a second warning position, WP2, a second line 147 appears along with the first line 146. At a third warning position, WP3, a third line 148 appears along with the first line 146 and the second line 147.

Similar to the embodiment illustrated in FIG. 9, also the embodiment illustrated in FIG. 10 provides the driver with three distinct warnings. In FIG. 10, the visual indication 140 is illustrated as solid, non-translucent, black lines, but may also be made translucent, frosted and with different colors, such as a distinct color for each line.

Figure 11:
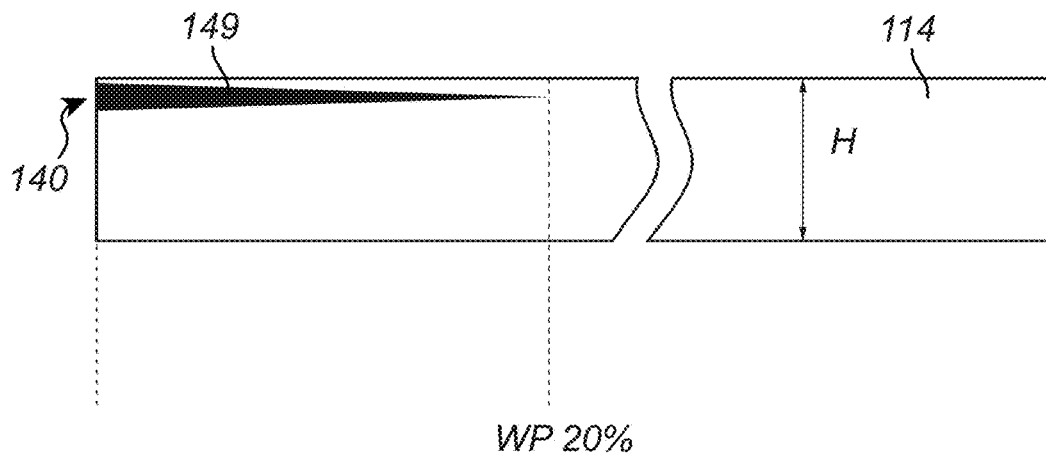
FIG. 11 is a front elevational view of an embodiment of a transparent film where the visual indication presents a continuously increasing height.

FIG. 11 illustrates an embodiment of the transparent film 114 where the visual indication 140 presents a continuously increasing height. The visual indication 140 is essentially an elongated triangle 149 extending in the longitudinal direction of the transparent film 114. A tip of the triangle 149 appears at the warning position, WP, and the triangle 149 extends towards the end of the film, such that the height of the visual indication 140 seen by the driver through the lens 105 grows larger as the end of the film 114 is approaching. The amount of film 114 left in the supply magazine 111 when the warning position WP appears in front of the lens 105 may last for essentially 15 full film advancements. The present arrangement provides a warning that continuously grows more visible, as the amount of film 114 left in the supply magazine 111 decreases. In FIG. 11, the visual indication 140 is illustrated as a solid, non-translucent, black triangle, but may also be made translucent, frosted and with different colors.

Figure 12:
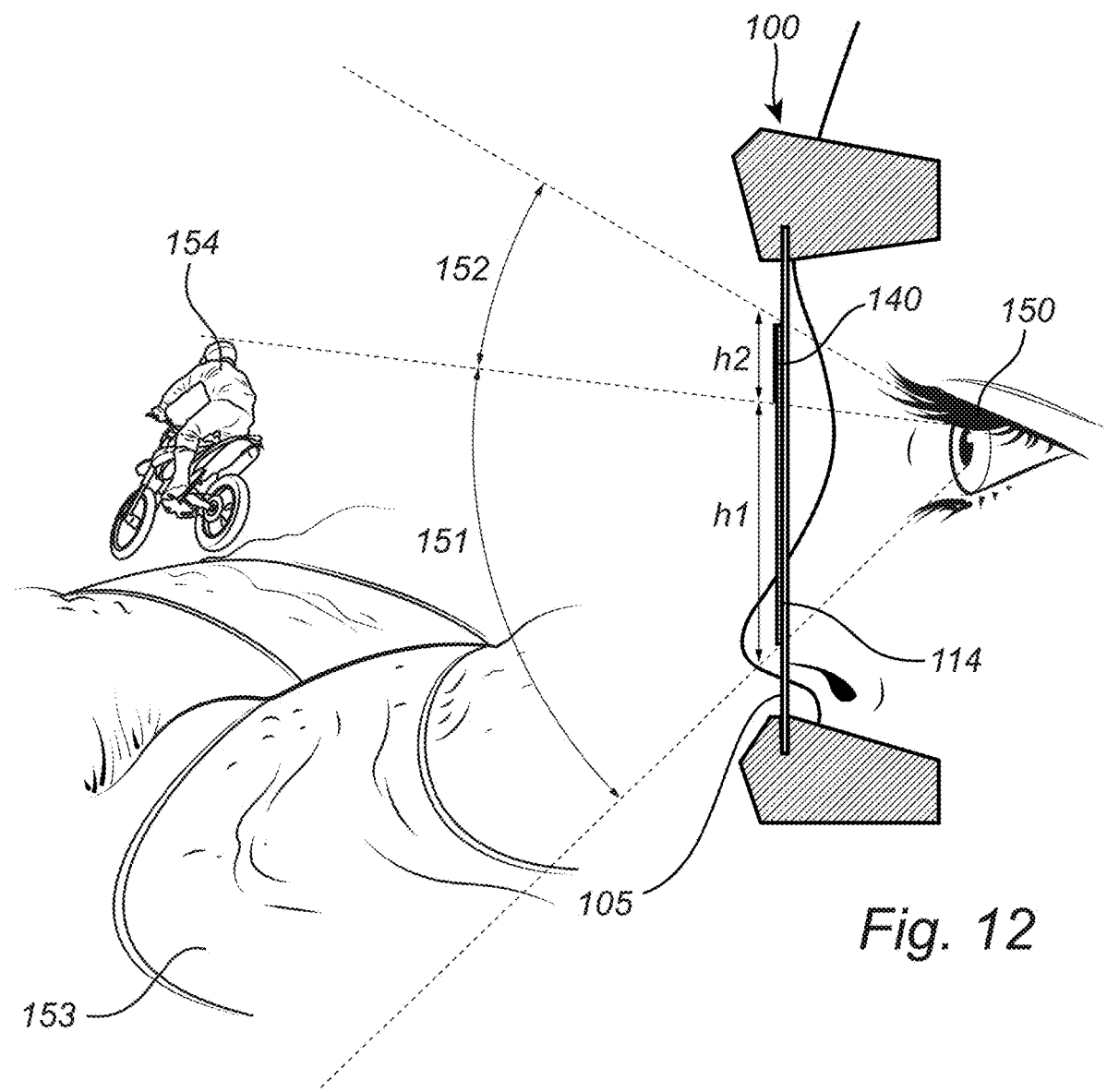
FIG. 12 is a vertical sectional view through a film advance system and film roll showing a primary and secondary field-of-view of a driver wearing a set of goggles including a film advance system and a film roll according to an embodiment of the invention.

FIG. 12 illustrates a field-of-view of the driver wearing a set of goggles 100 including a film advance system 110 and a film roll 113 according to an embodiment of the inventive concept. The goggles 100 are placed on the face of the driver such that the driver's eyes 150 are located behind the lens 105 and are thus protected from splashing mud, dirt or rocks. Looking through the lens 105, the driver has a primary field-of-view 151. The primary field-of-view 151 is where the driver needs to keep the eyes 150 during a major part of the race for keeping track of the path 153 where to drive, and of other drivers 154 in the race. Thus, the primary field-of-view 151 is substantially in the forward and downward directions from the driver's eyes 150 through the lens 105. The upward viewing direction, on the other hand, is not a viewing direction on which the driver needs to keep a major focus, and is here referred to as the secondary field-of-view 152. As the eyes are focusing in the primary field-of-view 151, the secondary field-of-view 152 is mostly seen by the driver's peripheral vision, and normally out of focus.

It is of importance to the driver to have unobstructed vision in the primary field-of-view 151. If the driver's vision is obstructed in the primary field-of-view 151, the driver may lose concentration or miss details in the surroundings or race track that may affect the driver's judgement and performance in the race. The transparent film 114 is arranged such that a main film part (h1) falls within the viewing direction of the primary field-of-view 151. This enables cleaning the primary field-of-view 151 from mud and dirt by advancing the film 114. As it is of importance to the driver to have unobstructed vision in the primary field-of-view 151, the visual indication 140 should preferably not appear in the primary field-of-view 151. Thus, the visual indication 140 should preferably not extend into the main film part defined by h1, being the central and bottom parts of the film 114. Therefore, arranging the visual indication 140 so that it only falls within the secondary field-of-view 152, thus in the region defined by h2, is preferred.

As also seen in FIG. 12, when the goggles 100 are worn by the driver, the visual indication 140 on the transparent film 114 is located so close to the driver's eyes 150 that the eyes may not be able to focus on the visual indication 140. This needs to be considered when designing the visual indication 140. For example, it is not likely that a driver would be able to read a written message on the film.

The invention has mainly been described above with reference to a few embodiments. However, as is readily appreciated by a person skilled in the art, other embodiments than the ones disclosed above are equally possible within the scope of the invention, as defined by the appended patent claims.

I claim:

1. A film roll for use in a film advance system for goggles used for eye protection, the film roll comprising:
   a spindle; and
   a transparent film being wound on the spindle and having a trailing end, a leading end, a height extending in a vertical direction, and a total film length extending in a longitudinal direction from the trailing end to the leading end, whereby in use the transparent film is arrangeable to extend across a lens of the goggles;
   wherein the transparent film has three planar parts, being:
   a main part which extends longitudinally over the total film length and vertically over a lower 50% of the height;
   an upper leading part which extends longitudinally from the leading end to a center of the total film length, and vertically over an upper 50% of the height;
   an upper trailing part which extends longitudinally from the center of the total film length to the trailing end, and vertically over an upper 50% of the height;
   wherein the main part has optically uniform characteristics at least in the longitudinal direction;
   wherein the upper trailing part has at least one visual indication that extends along an upper edge of the transparent film;
   wherein the at least one visual indication is transparent; and
   wherein the at least one visual indication is excluded from the main part and from the upper leading part.

2. The film roll according to claim 1, wherein the at least one visual indication has a total length along the upper edge which is less than 50% of the total film length.

3. The film roll according to claim 2, wherein the at least one visual indication has a total length that is less than 20% of the total film length.

4. The film roll according to claim 1, wherein the at least one visual indication extends continuously along the upper edge.

5. The film roll according to claim 4, wherein the at least one visual indication has a total visual indication length, and is a continuous line extending over the total visual indication length.

6. The film roll according to claim 4, wherein the at least one visual indication comprises a dashed line.

7. The film roll according to claim 4, wherein the at least one visual indication is at least in part a dotted line.

8. The film roll according to claim 1, wherein the at least one visual indication extends discontinuously along the upper edge.

9. The film roll according to claim 1, wherein the at least one visual indication is substantially uniform along a total length of the at least one visual indication.

10. The film roll according to claim 1, wherein the at least one visual indication has a constant height along a total length of the at least one visual indication.

11. The film roll according to claim 1, wherein the at least one visual indication has a height that varies along a total length of the at least one visual indication.

12. The film roll according to claim 1, wherein the at least one visual indication comprises a plurality of visual indications extending along the upper edge, and having mutually different total lengths.

13. The film roll according to claim 12, wherein the plurality of visual indications comprises a first visual indication and a second visual indication, wherein the second visual indication is shorter than the first visual indication, and the second visual indication is at least partly overlapping with the first visual indication.

14. The film roll according to claim 1, wherein the at least one visual indication is colored at least in part.

15. The film roll according to claim 14, wherein the at least one visual indication is red in at least in part.

16. The film roll according to claim 14, wherein the at least one visual indication is white at least in part.

17. The film roll according to claim 14, wherein the at least one visual indication, at least in part, has a color which varies along the at least one visual indication.

18. The film roll according to claim 1, wherein the at least one visual indication is applied onto a surface of the transparent film.

19. The film roll according to claim 1, wherein the at least one visual indication extends to the upper edge.

20. The film roll according to claim 19, wherein the at least one visual indication extends over the upper edge such that an edge part of the at least one visual indication is visible when the film roll is observed from a top side of the film roll.

21. The film roll according to claim 1, wherein the at least one visual indication has a height in a vertical direction of at least 35% of the height of the transparent film.

22. The film roll according to claim 1, wherein the upper leading part has optically uniform characteristics at least in the longitudinal direction.

23. A film advance system for goggles used for eye protection, the film advance system comprising:
   a film roll comprising:
      a spindle; and
      a transparent film being wound on the spindle and having a trailing end, a leading end, a height extending in a vertical direction, and a total film length extending in a longitudinal direction from the trailing end to the leading end, whereby in use the transparent film is arrangeable to extend across a lens of the goggles;
      wherein the transparent film has three planar parts, being:
      a main part which extends longitudinally over the total film length and vertically over a lower 50% of the height;
      an upper leading part which extends longitudinally from the leading end to a center of the total film length, and vertically over an upper 50% of the height;
      an upper trailing part which extends longitudinally from the center of the total film length to the trailing end, and vertically over an upper 50% of the height;
      wherein the main part has optically uniform characteristics at least in the longitudinal direction;
      wherein the upper trailing part has at least one visual indication that extends along an upper edge of the transparent film;
      wherein the at least one visual indication is transparent; and
      wherein the at least one visual indication is excluded from the main part and the upper leading part;

a supply magazine for the film roll, a take-up magazine, and an advance mechanism for advancing the transparent film of the film roll from the supply magazine to the take-up magazine.

24. The film advance system according to claim 23, wherein the at least one visual indication has a total length along the upper edge which is less than 50% of the total film length.

25. The film advance system according to claim 24, wherein the at least one visual indication has a total length that is less than 20% of the total film length.

26. The film advance system according to claim 23, wherein the at least one visual indication extends continuously along the upper edge.

27. The film advance system according to claim 26, wherein the at least one visual indication comprises a continuous line extending over a total length of the at least one visual indication.

28. The film advance system according to claim 26, wherein the at least one visual indication comprises a dashed line.

29. The film advance system according to claim 26, wherein the at least one visual indication is at least in part a dotted line.

30. The film advance system according to claim 25, wherein the at least one visual indication extends discontinuously along the upper edge.

31. The film advance system according to claim 23, wherein the at least one visual indication is substantially uniform along a total length of the at least one visual indication.

32. The film advance system according to claim 23, wherein the at least one visual indication has a constant height along a total length of the at least one visual indication.

33. The film advance system according to claim 23, wherein the at least one visual indication has a height that varies along a total length of the at least one visual indication.

34. The film advance system according to claim 23, wherein the at least one visual indication comprises a plurality of visual indications extending along the upper edge, and having mutually different total lengths.

35. The film advance system according to claim 34, wherein the plurality of visual indications comprises a first visual indication and a second visual indication, wherein the second visual is shorter than the first visual indication, and the second visual indication is at least partly overlapping with the first visual indication.

36. The film advance system according to claim 23, wherein the at least one visual indication is colored at least in part.

37. The film advance system according to claim 36, wherein the at least one visual indication is red in at least in part.

38. The film advance system according to claim 36, wherein the at least one visual indication is white at least in part.

39. The film advance system according to claim 36, wherein the at least one visual indication, at least in part, has a color which varies along the at least one visual indication.

40. The film advance system according to claim 23, wherein the at least one visual indication is applied onto a surface of the transparent film.

41. The film advance system according to claim 23, wherein the at least one visual indication extends to the upper edge.

42. The film advance system according to claim 41, wherein the at least one visual indication extends over the upper edge such that an edge part of the at least one visual indication is visible when the film roll is observed from a top side of the film roll.

43. The film advance system according to claim 23, wherein the at least one visual indication has a height in the vertical direction of at least 35% of the height of the transparent film.

44. The film advance system according to claim 23, wherein the upper leading part has optically uniform characteristics at least in the longitudinal direction.

* * * * *